(12) United States Patent
Goulet et al.

(10) Patent No.: US 6,197,975 B1
(45) Date of Patent: Mar. 6, 2001

(54) ANTAGONISTS OF GONADOTROPIN RELEASING HORMONE

(75) Inventors: Mark Goulet, Westfield; Wallace T. Ashton, Clark; Lin Chu, Scotch Plains; Michael H. Fisher, Ringoes; Matthew J. Wyvratt, Mountainside, all of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/077,565

(22) PCT Filed: Dec. 10, 1996

(86) PCT No.: PCT/US96/19767

§ 371 Date: Jun. 1, 1998

§ 102(e) Date: Jun. 1, 1998

(87) PCT Pub. No.: WO97/21707

PCT Pub. Date: Jun. 19, 1997

Related U.S. Application Data

(63) Continuation of application No. 08/760,866, filed on Dec. 5, 1996, now abandoned.
(60) Provisional application No. 60/008,631, filed on Dec. 14, 1995.

(30) Foreign Application Priority Data

Feb. 16, 1996 (GB) .................................................. 9603344

(51) Int. Cl.[7] ..................... C07D 403/12; C07D 405/12; A61K 31/40
(52) U.S. Cl. .......................... 548/453; 548/453; 548/454; 514/413; 514/414
(58) Field of Search .................................. 548/453, 454; 514/413

(56) References Cited

U.S. PATENT DOCUMENTS

| | | | |
|---|---|---|---|
| 4,139,634 | 2/1979 | Pigerol et al. | 424/274 |
| 4,252,803 | 2/1981 | Webb | 424/248.5 |
| 4,544,663 | 10/1985 | Manning et al. | 514/378 |
| 4,943,572 | 7/1990 | von Angerer | 514/235.2 |
| 5,030,640 | 7/1991 | Fisher et al. | 514/339 |
| 5,756,507 | 5/1998 | Goulet et al. | 514/255 |
| 5,780,437 | 7/1998 | Goulet et al. | 514/19 |

FOREIGN PATENT DOCUMENTS

| | | |
|---|---|---|
| 0 219 292 A2 | 4/1987 | (EP) . |
| 0 679 642 A1 | 11/1995 | (EP) . |
| WO90/05721 | 5/1990 | (WO) . |
| 9510513 * | 4/1995 | (WO) ................................ 333/56 |
| WO95/28405 | 10/1995 | (WO) . |
| WO95/29900 | 11/1995 | (WO) . |

OTHER PUBLICATIONS

J. Med. Chem., vol. 32, No. 9, pp. 2036–2038 (1989), by Biswanath De, et al.
CA 80:108368, FR 2181559, by Boch, et al. (No 8F. in Abstract, Need the Whole Document).

* cited by examiner

Primary Examiner—Jose' G. Dees
(74) Attorney, Agent, or Firm—Elliott Korsen; Mark R. Daniel

(57) ABSTRACT

There are disclosed compounds of formula (I) and pharmaceutically acceptable salts thereof which are useful as antagonists of GnRH and as such may be useful for the treatment of a variety of sex-hormone related and other conditions in both men and women.

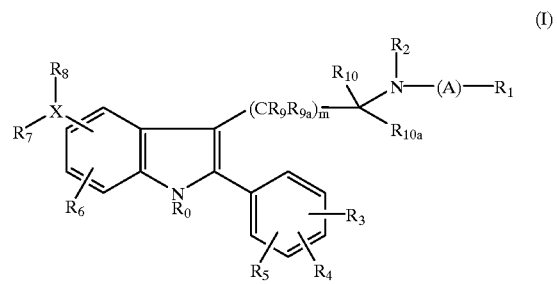

(I)

19 Claims, No Drawings

ANTAGONISTS OF GONADOTROPIN RELEASING HORMONE

This application claims benefit of Provisional 06/008,631, filed Dec. 14, 1995, and continuation of Ser. No. 08/760,866, filed Dec. 5, 1996, now abandoned.

BACKGROUND OF THE INVENTION

The gonadotropin-releasing hormone (GnRH), also referred to as luteinizing hormone-releasing hormone (LHRH), is a decapeptide that plays a key role in human reproduction. The hormone is released from the hypothalamus and acts on the pituitary gland to stimulate the biosynthesis and secretion of luteinizing hormone (LH) and follicle-stimulating hormone (FSH). LH released from the pituitary gland is primarily responsible for the regulation of gonadal steroid production in both sexes, whereas FSH regulates spermatogenesis in males and follicular development in females. GnRH agonists and antagonists have proven effective in the treatment of certain conditions which require inhibition of LP/FSH release. In particular, GnRH-based therapies have proven effective in the treatment of endometriosis, uterine fibroids, polycystic ovarian disease, precocious puberty and several gonadal steroid-dependent neoplasia, most notably cancers of the prostate, breast and ovary. GnRH agonists and antagonists have also been utilized in various assisted fertilization techniques and have been investigated as a potential contraceptive in both men and women. They have also shown possible utility in the treatment of pituitary gonadotrophe adenomas, sleep disorders such as sleep apnea, irritable bowel syndrome, premenstrual syndrome, benign prostatic hyperplasia, hirsutism, as an adjunct to growth hormone therapy in growth hormone deficient children, and in murine models of lupus. The compounds of the invention may also be used in combination with bisphosphonates (bisphosphonic acids) and other agents, such as growth hormone secretagogues, e.g. MK-0677, for the treatment and the prevention of disturbances of calcium, phosphate and bone metabolism, in particular, for the prevention of bone loss during therapy with the GnRH antagonist, and in combination with estrogens, progesterones, antiestrogens, antiprogestins and/or androgens for the prevention or treatment of bone loss or hypogonadal symptoms such as hot flashes during therapy with the GnRH antagonist.

Additionally, a compound of the present invention may be co-administered with a 5α-reductase 2 inhibitor, such as finasteride or epristeride; a 5α-reductase 1 inhibitor such as 4,7β-dimethyl-4-aza-5α-cholestan-3-one, 3-oxo-4-aza-4,7β-dimethyl-16β-(4-chlorophenoxy)-5α-androstane, and 3-oxo-4-aza4,7β-dimethyl-16β-(phenoxy)-5α-androstane as disclosed in WO 93123420 and WO 95/11254; dual inhibitors of 5α-reductase 1 and 5α-reductase 2 such as 3-oxo-4-aza-17β-(2,5-trifluoromethylphenyl-carbamoyl)-5α-androstane as disclosed in WO 95/07927; antiandrogens such as flutamide, casodex and cyproterone acetate, and alpha-1 blockers such as prazosin, terazosin, doxazosin, tamsulosin, and alfuzosin.

Further, a compound of the present invention may be used in combination with growth hormone, growth hormone releasing hormone or growth hormone secretagogues, to delay puberty in growth hormone deficient children, which will allow them to continue to gain height before fusion of the epiphyses and cessation of growth at puberty.

Current GnRH antagonists are GnRH-like decapeptides which are generally administered intravenously or subcutaneously presumably because of negligible oral activity. These have amino acid substitutions usually at positions one, two, three, six and ten.

Non-peptide GnRH antagonists offer the possible advantage of oral adminstration. Non-peptide GnRH antagonists have been described in European Application 0 219 292 and in De, B. et al., J. Med. Chem., 32, 2036–2038 (1989), in WO 95/28405, WO 95/29900 and EP 0679642 all to Takeda Chemical Industries, Ltd.

Substituted indoles known in the art include those described in the following patents and patent applications. U.S. Pat. No. 5,030,640 discloses alpha-heterocyclic ethanol aminoalkyl indoles which are potent β-agonists. U.S. Pat. No. 4,544,663 discloses indolamine derivatives which are allegedly useful as male anti-fertility agents. WO 90/05721 discloses alpha-amino-indole-3-acetic acids useful as anti-diabetic, anti-obesity and anti-atherosclerotic agents. French patent 2,181,559 discloses indole derivatives with sedative, neuroleptic, analgesic, hypotensive, antiserotonin and adrenolytic activity. Belgian patent 879381 discloses 3-aminoalkyl-1H-indole-5-thioamide and carboxamide derivatives as cardiovascular agents used to treat hypertension, Raynaud's disease and migraine.

SUMMARY OF THE INVENTION

The present invention relates to compounds which are non-peptide antagonists of GnRH which can be used to treat a variety of sex-hormone related conditions in men and women, to methods for their preparation, and to methods and pharmaceutical compositions containing said compounds for use in mammals.

Because of their activity as antagonists of the hormone GnRH, the compounds of the present invention are useful to treat a variety of sex-hormone related conditions in both men and women. These conditions include endometriosis, uterine fibroids, polycystic ovarian disease, hirsutism, precocious puberty, gonadal steroid-dependent neoplasias such as cancers of the prostate, breast and ovary, gonadotrophe pituitary adenomas, sleep apnea, irritable bowel syndrome, premenstrual syndrome and benign prostatic hypertophy. They are also useful as an adjunct to treatment of growth hormone deficiency and short stature, and for the treatment of systemic lupus erythematosis. Further, the compounds of the invention may be useful in in vitro fertilization and as contraceptives. The compounds may also be useful in combination with androgens, estrogens, progesterones, antiestrogens and antiprogestogens for the treatment of endometriosis, fibroids and in contraception. They may also be useful in combination with testosterone or other androgens or antiprogestogens in men as a contraceptive. The compounds may also be used in combination with an angiotensin-converting enzyme inhibitor such as Enalapril or Captopril, an angiotensin II-receptor antagonist such as Losartan or a renin inhibitor for the treatment of uterine fibroids. Additionally, the compounds of the invention may also be used in combination with bisphosphonates (bisphosphonic acids) and other agents, for the treatment and the prevention of disturbances of calcium, phosphate and bone metabolism, in particular, for the prevention of bone loss during therapy with the GnRH antagonist, and in combination with estrogens, progesterones and or androgens for the prevention or treatment of bone loss or hypogonadal symptoms such as hot flashes during therapy with the GnRH antagonist.

Additionally, a compound of the present invention may be co-administered with a 5α-reductase 2 inhibitor, such as finasteride or epristeride; a 5α-reductase 1 inhibitor such as 4,7β-dimethyl-4-aza-5α-cholestan-3-one, 3-oxo-4-aza4,7β-dimethyl- 16β-(4-chlorophenoxy)-5α-androstane, and 3-oxo-4-aza-4,7β-dimethyl-16β-(phenoxy)-5α-androstane as disclosed in WO 93/23420 and WO 95/111254; dual inhibitors of 5α-reductase 1 and 5α-reductase 2 such as 3-oxo4-aza-17β-(2,5-trifluoromethylphenyl-carbamoyl)-5α-androstane as disclosed in WO 95/07927; antiandrogens such as flutamide, casodex and cyproterone acetate, and alpha-1 blockers such as prazosin, terazosin, doxazosin, tamsulosin, and alfuzosin.

Further, a compound of the present invention may be used in combination with growth hormone, growth hormone releasing hormone or growth hormone secretagogues, to delay puberty in growth hormone deficient children, which will allow them to continue to gain height before fusion of the epiphyses and cessation of growth at puberty.

DETAILED DESCRIPTION OF THE INVENTION

The present invention relates to compounds of the general formula

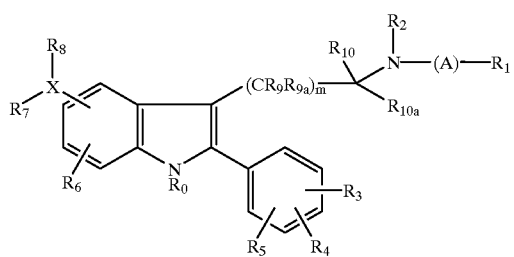

(I)

wherein

A is $C_1-C_6$ alkyl, substituted $C_1-C_6$ alkyl, $C_3-C_7$ cycloalkyl, substituted $C_3-C_7$ cycloalkyl, $C_3-C_6$ alkenyl, substituted $C_3-C_6$ alkenyl, $C_3-C_6$ alkynyl, substituted $C_3-C_6$ alkynyl, $C_1-C_6$ alkoxy, or $C_0-C_5$ alkyl-$S(O)_n$-CO-$C_5$ alkyl, $C_0-C_5$ alkyl-O-$C_0-C_5$ alkyl, $C_0-C_5$ alkyl-$NR_{18}$-$C_0-C_5$ alkyl where $R_{18}$ and the $C_0-C_5$ alkyl can be joined to form a ring,

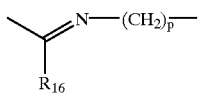, or a single bond.

$R_0$ is hydrogen, $C_1-C_6$ alkyl, substituted $C_1-C_6$ alkyl, wherein the substituents are as defined below; aryl, substituted aryl, aralkyl or substituted aralkyl, wherein the substituents are as defined for $R_3$, $R_4$ and $R_5$.

$R_1$ is

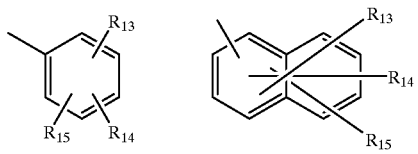

-continued

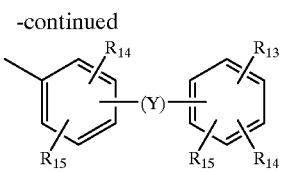

wherein:
Y is B, C or a bond;
B is O, $S(O)_n$, C(O), $NR_{18}$ or $C(R_{11}R_{12})_p$
C is $B(CH_2)_p$—;
$R_2$ is hydrogen, $C_1-C_6$ alkyl, substituted $C_1-C_6$ alkyl, aralkyl, substituted aralkyl, aryl, substituted aryl, alkyl —$OR_{11}$, $C_1-C_6(NR_{11}R_{12})$, $C_1-C_6(CONR_{11}R_{12})$ or $C(NR_{11}R_{12})NH$;
$R_2$ and A taken together form a ring of 5–7 atoms;
$R_3$, $R_4$ and $R_5$ are independently hydrogen, $C_1-C_6$ alkyl, substituted $C_1-C_6$ alkyl, $C_2-C_6$ alkenyl, substituted $C_2-C_6$ alkenyl, CN, nitro, $C_1-C_3$ perfluoroalkyl, $C_1-C_3$ perfluoroalkoxy, aryl, substituted aryl, aralkyl, substituted aralkyl, $R_{11}O(CH_2)_p$—, $R_{11}C(O)O(CH_2)_p$—, $R_{11}OC(O)(CH_2)_p$—, —$(CH_2)_pS(O)_nR_{17}$, —$(CH_2)_pC(O)NR_{11}R_{12}$ or halogen; wherein $R_{17}$ is hydrogen, $C_1-C_6$ alkyl, $C_1-C_3$ perfluoroalkyl, aryl or substituted aryl;
$R_3$ and $R_4$ taken together form a carbocyclic ring of 3–7 carbon atoms or a heterocyclic ring containing 1–3 heteroatoms selected from N, O and S;
$R_6$ is hydrogen, $C_1-C_6$ alkyl, substituted $C_1-C_6$ alkyl, aryl, substituted aryl, $C_1-C_3$ perfluoroalkyl, CN, $NO_2$, halogen, $R_{11}O(CH_2)_p$—, $NR_{21}C(O)R_{20}$, $NR_{21}C(O)NR_{20}R_{21}$ or $SO_nR_{20}$;
$R_7$ is hydrogen, $C_1-C_6$ alkyl, or substituted $C_1-C_6$ alkyl, unless X is hydrogen or halogen, then $R_7$ is absent;
$R_8$ is $C(O)OR_{20}$, $C(O)NR_2R_{21}$, $NR_{20}R_{21}$, $C(O)R_{20}$, $NR_{21}C(O)R_{20}$, $NR_{21}C(O)NR_{20}R_{21}$, $NR_{20}S(O)_2R_{21}$, $NR_{21}S(O)_2NR_{20}R_{21}$, $OC(O)R_{20}$, $OC(O)NR_{20}R_{21}$, $OR_{20}$, $SO_nR_{20}$, $S(O)_nNR_{20}R_{21}$, a heterocyclic ring or bicyclic heterocyclic ring with from 1 to 4 heteroatoms selected from N, O or S which can be optionally substituted by $R_3$, $R_4$ and $R_5$, $C_1-C_6$ alkyl or substituted $C_1-C_6$ alkyl; or
$R_7$ and $R_8$ taken together form a heterocyclic ring containing one or more heteroatoms selected from N, O or S which can be optionally substituted by $R_3$, $R_4$ and $R_5$;
$R_9$ and $R_{9a}$ are independently hydrogen, $C_1-C_6$ alkyl, substituted $C_1-C_6$ alkyl; aryl or substituted aryl, aralkyl or substituted aralkyl when m 0; or
$R_9$ and $R_{9a}$ taken together form a carbocyclic ring of 3–7 atoms or

when m 0;
$R_9$ and A taken together form a heterocyclic ring containing 3–7 carbon atoms and one or more heteroatoms when m 0; or
$R_{10}$ and $R_{10a}$ are independently hydrogen, $C_1-C_6$ alkyl, substituted $C_1-C_6$ alkyl, aryl, substituted aryl, aralkyl or substituted aralkyl; or
$R_{10}$ and $R_{10a}$ taken together form a carbocyclic ring of 3–7 atoms or

$R_9$ and $R_{10}$ taken together form a carbocyclic ring of 3–7 carbon atoms or a heterocyclic ring containing one or more heteroatoms when m 0; or $R_9$ and $R_2$ taken together form a heterocyclic ring containing 3–7 carbon atoms and one or more heteroatoms when m 0; or $R_{10}$ and $R_2$ taken together form a heterocyclic ring containing 3–7 carbon atoms and one or more heteroatoms;

$R_{10}$ and A taken together form a heterocyclic ring containing 3–7 carbon atoms and one or more heteroatoms; or $R_{11}$ and $R_{12}$ are independently hydrogen, $C_1$–$C_6$ alkyl, substituted $C_1$–$C_6$ alkyl, aryl, substituted aryl, aralkyl, substituted aralkyl, a carbocyclic ring of 3–7 atoms or a substituted carbocyclic ring containing 3–7 atoms;

$R_{11}$ and $R_{12}$ taken together can form an optionally substituted ring of 3–7 atoms;

$R_{13}$ is hydrogen, OH, $NR_7R_8$, $NR_{11}SO_2(C_1$–$C_6$ alkyl), $NR_{11}SO_2$(substituted $C_1$–$C_6$ alkyl), $NR_{11}SO_2$(aryl), $NR_{11}SO_2$(substituted aryl), $NR_{11}SO_2(C_1$–$C_3$ perfluoroalkyl); $SO_2NR_{11}(C_1$–$C_6$ alkyl), $SO_2NR_{11}$ (substituted $C_1$–$C_6$ alkyl), $SO_2NR_{11}$(aryl), $SO_2NR_{11}$ (substituted aryl), $SO_2NR_{11}(C_1$–$C_3$ perfluoroalkyl); $SO_2NR_{11}(C(O)C_1$–$C_6$ alkyl); $SO_2NR_{11}(C(O)$-substituted $C_1$–$C_6$ alkyl); $SO_2NR_{11}(C(O)$-aryl); $SO_2NR_{11}(C(O)$-substituted aryl); $S(O)_n(C_1$–$C_6$ alkyl); $S(O)_n$ (substituted $C_1$–$C_6$ alkyl), $S(O)_n$(aryl), $S(O)_n$(substituted aryl), $C_1$–$C_3$ perfluoroalkyl, $C_1$–$C_3$ perfluoroalkoxy, $C_1$–$C_6$ alkoxy, substituted $C_1$–$C_6$ alkoxy, COOH, halogen, $NO_2$ or CN;

$R_{14}$ and $R_{15}$ are independently hydrogen, $C_1$–$C_6$ alkyl, substituted $C_1$–$C_6$ alkyl, $C_2$–$C_6$ alkenyl, substituted $C_2$–$C_6$ alkenyl, CN, nitro, $C_1$–$C_3$ perfluoroalkyl, $C_1$–$C_3$ perfluoroalkoxy, aryl, substituted aryl, aralkyl, substituted aralkyl, $R_{11}O(CH_2)_p$—, $R_{11}C(O)O(CH_2)_p$—, $R_{11}OC(O)(CH_2)_p$—, —$(CH_2)_pS(O)_nR_{17}$, —$(CH_2)_pC(O)NR_{11}R_{12}$ or halogen; wherein $R_{17}$ is hydrogen, $C_1$–$C_6$ alkyl, $C_1$–$C_3$ perfluoroalkyl, aryl or substituted aryl;

$R_{16}$ is hydrogen, $C_1$–$C_6$ alkyl, substituted $C_1$–$C_6$ alkyl, or $N(R_{11}R_{12})$;

$R_{18}$ is hydrogen, $C_1$–$C_6$ alkyl, substituted $C_1$–$C_6$ alkyl, $C(O)OR_{11}$, $C(O)NR_{11}R_{12}$, $C(O)R_{11}$, $S(O)_nR_{11}$;

$R_{20}$ and $R_{21}$ are independently hydrogen, $C_1$–$C_6$ alkyl, substituted $C_1$–$C_6$ alkyl, aryl, substituted aryl, aralkyl, substituted aralkyl, a carbocyclic ring of 3–7 atoms, a substituted carbocyclic ring containing 3–7 atoms, a heterocyclic ring or bicyclic heterocyclic ring with from 1 to 4 heteroatoms selected from N, O or S which can be optionally substituted by $R_3$, $R_4$ and $R_5$, $C_1$–$C_6$-alkyl substituted by a heterocyclic ring or bicyclic heterocyclic ring with from 1 to 4 heteroatoms selected from N, O or S which can be optionally substituted by $R_3$, $R_4$ and $R_5$;

$R_{20}$ and $R_{21}$ taken together can form an optionally substituted ring of 3–7 atoms;

X is N, O, $S(O)_n$, C(O), $(CR_{11}R_{12})_p$, a single bond to $R_8$, $C_2$–$C_6$ alkenyl, substituted $C_2$–$C_6$ alkenyl, $C_2$–$C_6$ alkynyl, or substituted $C_2$–$C_6$ alkynyl; when X is O, S(O)n, C(O), or $CR_{11}R_{12}$ only $R_8$ is possible;

m is 0–3;

n is 0–2;

p is 0–4; and the alkyl, cycloalkyl, alkenyl and alkynyl substituents are selected from $C_1$–$C_6$ alkyl, $C_3$–$C_7$ cycloalkyl, aryl, substituted aryl, aralkyl, substituted aralkyl, hydroxy, oxo, cyano, $C_1$–$C_6$ alkoxy, fluoro, $C(O)OR_{11}$, $C_1$–$C_3$ alkoxy, substituted aryl $C_1$–$C_3$ alkoxy, and the aryl substituents are as defined for $R_3$, $R_4$ and $R_5$;

or a pharmaceutically acceptable addition salt and/or hydrate thereof, or where applicable, a geometric or optical isomer or racemic mixture thereof.

Unless otherwise stated or indicated, the following definitions shall apply throughout the specification and claims.

When any variable (e.g., aryl, heterocycle, $R_1$, etc.) occurs more than one time in any constituent or in formula I, its definition on each occurrence is independent of its definition at every other occurrence. Also, combinations of substituents and/or variables are permissible only if such combinations result in stable compounds.

The term "alkyl" is intended to include both branched- and straight-chain saturated aliphatic hydrocarbon groups having the specified number of carbon atoms, e.g., methyl (Me), ethyl (Et), propyl, butyl, pentyl, hexyl, heptyl, octyl, nonanyl, decyl, undecyl, dodecyl, and the isomers thereof such as isopropyl (i-Pr), isobutyl (i-Bu), sec-butyl (s-Bu), tert-butyl (t-Bu), isopentane, isohexane, etc.

The term "aryl" includes phenyl and naphthyl. Preferably, aryl is phenyl.

The term "halogen" or "halo" is intended to include fluorine, chlorine, bromine and iodine.

The term "heterocycle" or "heterocyclic ring" is defined by all non-aromatic, heterocyclic rings of 3–7 atoms containing 1–3 heteroatoms selected from N, O, and S, such as oxirane, oxetane, tetrahydrofuran, tetrahydropyran, pyrrolidine, piperidine, tetrahydropyridine, tetrahydropyrimidine, tetrahydrothiophene, tetrahydrothiopyran, morpholine, hydantoin, valerolactam, pyrrolidinone, and the like.

As used herein, the term "composition" is intended to encompass a product comprising the specified ingredients in the specified amounts, as well as any product which results, directly or indirectly, from combination of the specified ingredients in the specified amounts In addition, it is well known to those skilled in the art that many of the foregoing heterocyclic groups can exist in more than one tautomeric form. It is intended that all such tautomers be included within the ambit of this invention.

The optical isomeric forms, that is mixtures of enantiomers, e.g., racemates, or diastereomers as well as individual enantiomers or diastereomers of the instant compound are included. These individual enantiomers are commonly designated according to the optical rotation they effect by the symbols (+) and (−), (L) and (D), (l) and (d) or combinations thereof. These isomers may also be designated according to their absolute spatial configuration by (S) and (R), which stands for sinister and rectus, respectively.

The individual optical isomers may be prepared using conventional resolution procedures, e.g., treatment with an appropriate optically active acid, separating the diastereomers and then recovering the desired isomer. In addition, the individual optical isomers may be prepared by asymmetric synthesis.

Additionally, a given chemical formula or name shall encompass pharmaceutically acceptable addition salts thereof and solvates thereof, such as hydrates.

The compounds of the present invention, while effective themselves, may be formulated and administered in the form of their pharmaceutically acceptable addition salts for purposes of stability, convenience of crystallization, increased solubility and other desirable properties.

The compounds of the present invention may be administered in the form of pharmaceutically acceptable salts. The term "pharmaceutically acceptable salt" is intended to include all acceptable salts. Examples of acid salts are hydrochloric, nitric, sulfuric, phosphoric, formic, acetic, trifluoroacetic, propionic, maleic, succinic, malonic, methane sulfonic and the like which can be used as a dosage form for modifying the solubility or hydrolysis characteristics or can be used in sustained release or prodrug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, omithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, e.g. by reacting a free acid with a suitable organic or inorganic base, or alternatively by reacting a free base with a suitable organic or inorganic acid.

Also, in the case of an acid (—COOH) or alcohol group being present, pharmaceutically acceptable esters can be employed, e.g. methyl, ethyl, butyl, acetate, maleate, pivaloyloxymethyl, and the like, and those esters known in the art for modifying solubility or hydrolysis characteristics for use as sustained release or prodrug formulations.

The compounds of the present invention may have chiral centers other than those centers whose stereochemistry is depicted in formula I, and therefore may occur as racemates, racemic mixtures and as individual enantiomers or diastereomers, with all such isomeric forms being included in the present invention as well as mixtures thereof. Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

The compounds of the invention are prepared by the following reaction schemes. All substituents are as defined above unless indicated otherwise.

Scheme A

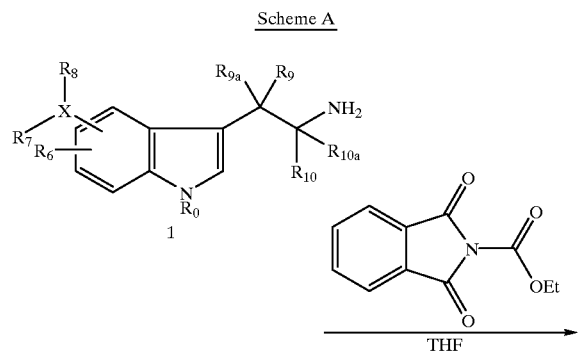

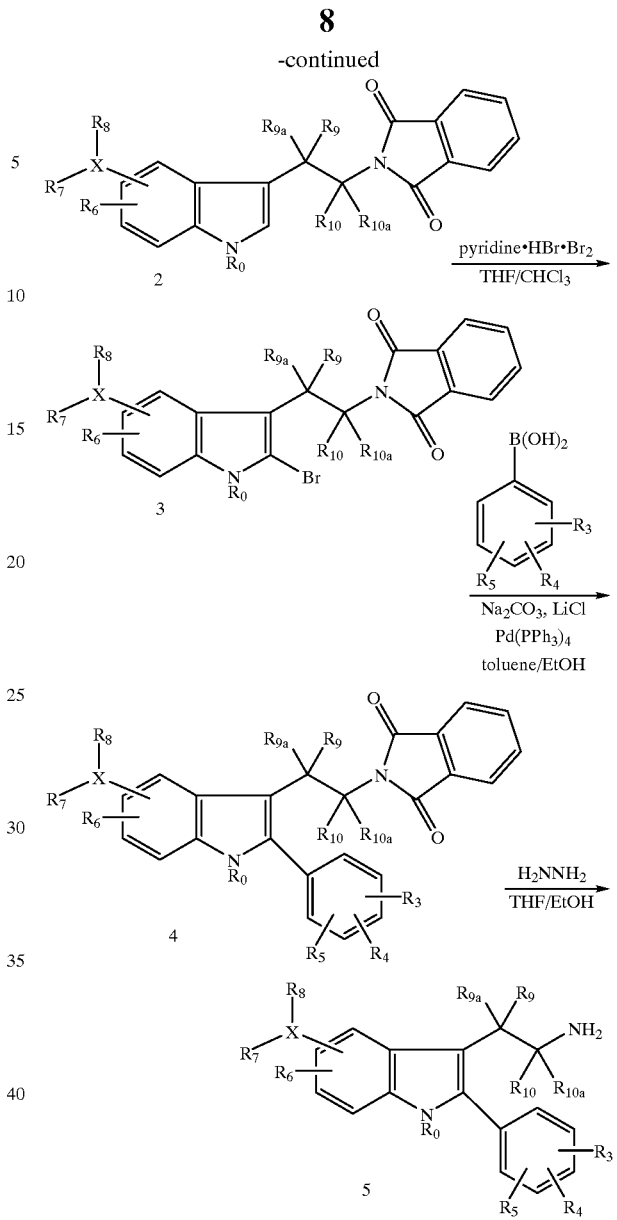

Reaction Scheme A

As shown in reaction Scheme A, treatment of tryptamine (1) with N-carboxyphthalimide in an inert organic solvent such as tetrahydrofuran at a temperature of 20°–65° C., preferably 65° C., for a period of 12–48 hours gives the corresponding N-phthalimidotryptamine derivative (2). The N-phthalimidotryptamine (2) could be further modified by treatment with a brominating agent such as pyridinium hydrobromide perbromide, pyrrolidone hydrotribromide, or the like in an inert organic solvent such as tetrahydrofuran, methylene chloride, chloroform, or mixtures thereof at 0°–25° C. for a period of 30 minutes to 4 hours to provide the 2-bromotryptamine (3). Bromide (3) may be reacted with an arylboronic acid (prepared essentially as described in: Gronowitz, S.; Hornfeldt, A.-B.; Yang, Y.-H. *Chem. Scr.* 1986,26, 311–314.) with palladium (O) catalysis, a weak base such as aqueous sodium carbonate or the like, and a chloride source such as lithium chloride in an inert solvent like toluene, benzene, ethanol, propanol or mixtures thereof at a temperature of 25°–100° C., preferably 80° C., for a period of 1–6 hours to give the 2-aryltryptamine derivative (4). Finally, the phthalimido group may be removed by treatment of (4) with aqueous hydrazine in an inert solvent such as methanol or ethanol at a temperature of 0°–25° C. for a period of 4–24 hours to give tryptamine (5).

Scheme B

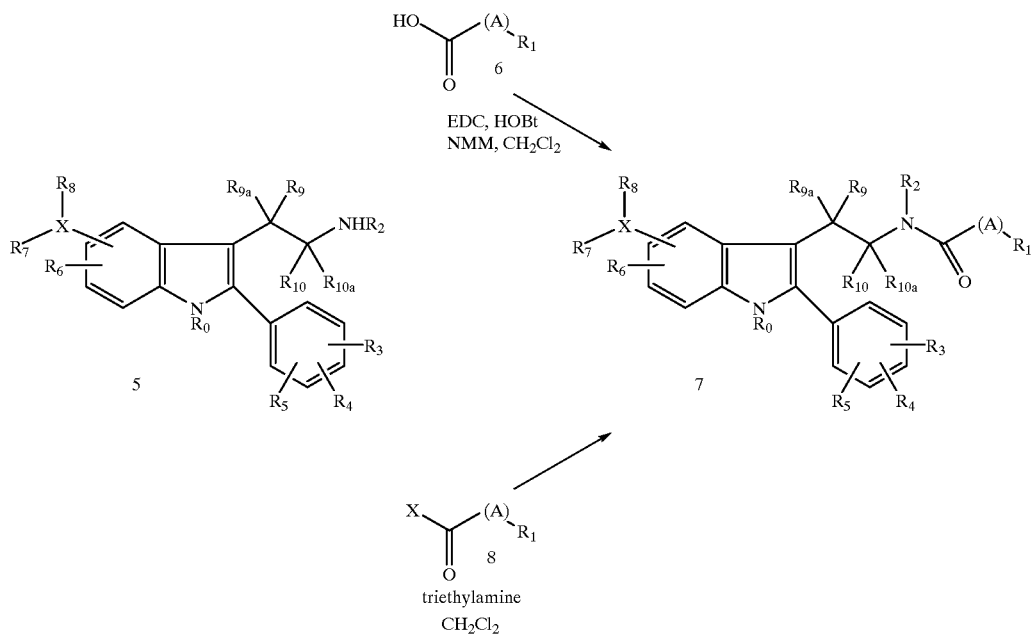

Reaction Scheme B

As shown in reaction Scheme B the 2-aryltryptamine may be condensed with a carboxylic acid of type (6) using the coupling reagent 1-(3-dimethylaminopropyl)-3-ethylcarbodiimide hydrochloride (EDC), 1,3-dicyclohexylcarbodiimide (DCC) or the like with or without 1-hydroxybenzotriazole (HOBt) and a tertiary amine base such as N-methylmorpholine (NMM), triethylamine or the like in an inert organic solvent such as methylene chloride, chloroform, dimethylformamide, or mixtures thereof at or near room temperature for a period of 3–24 hours to provide the corresponding amide derivative (7). Alternatively, 2-aryltryptamine (5) can be treated with an active ester or acid chloride of type (8) in an inert organic solvent such as methylene chloride, chloroform, tetrahydrofuran, diethyl ether, or the like and a tertiary amine base such as triethylamine, diisopropylethylamine, pyridine or the like at a temperature of 0°–25° C. for 30 minutes to 4 hours to give (7).

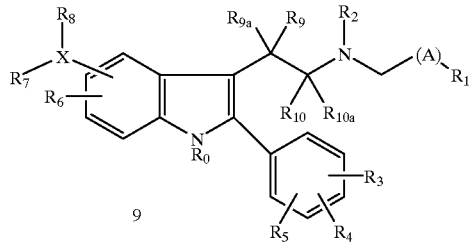

Reaction Scheme C

As shown in reaction Scheme C the amide carbonyl of (7) can be reduced by treatment with borane, lithium aluminum hydride, or equivalent hydride sources in an inert organic solvent such as tetrahydrofuran, diethyl ether, 1,4-dioxane or the like at 25°–100° C., preferably 65° C., for a period of 1–8 hours to give the corresponding amine compound (9).

Scheme C

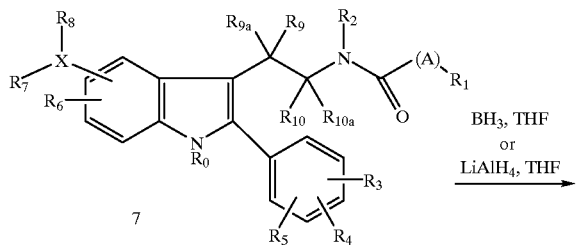

Scheme D

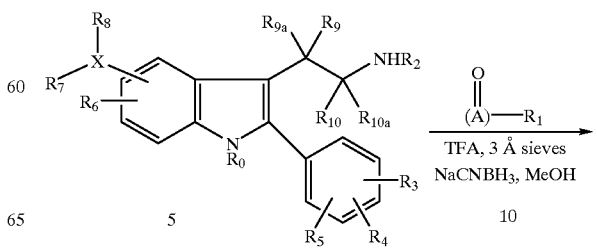

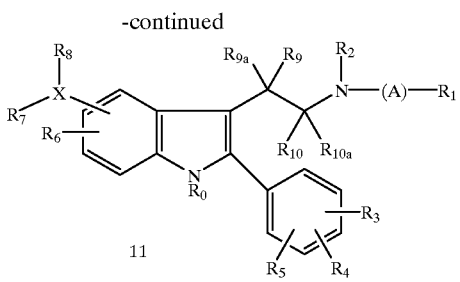

11

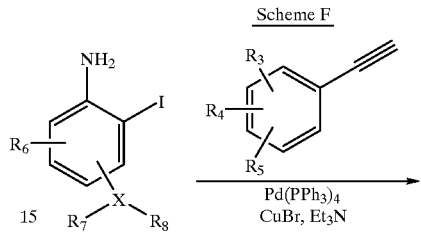

Reaction Scheme D

As shown in reaction Scheme D the 2-aryltryptamine (5) can be modified by treatment with an aldehyde or ketone of type (10) in the presence of a weak acid such as trifluorfoacetic acid (TFA), acetic acid or the like, with or without a dessicant such as 3Å molecular sieves or magnesium sulfate, and a hydride source such as sodium borohydride or sodium cyanoborohydride, in an inert organic solvent such as methanol, ethanol, isopropanol, tetrahydrofuran, dichloromethane, chloroform, or mixtures thereof at a temperature of 0°–25° C. for a period of 1–12 hours to give the corresponding secondary or tertiary amine derivative (11).

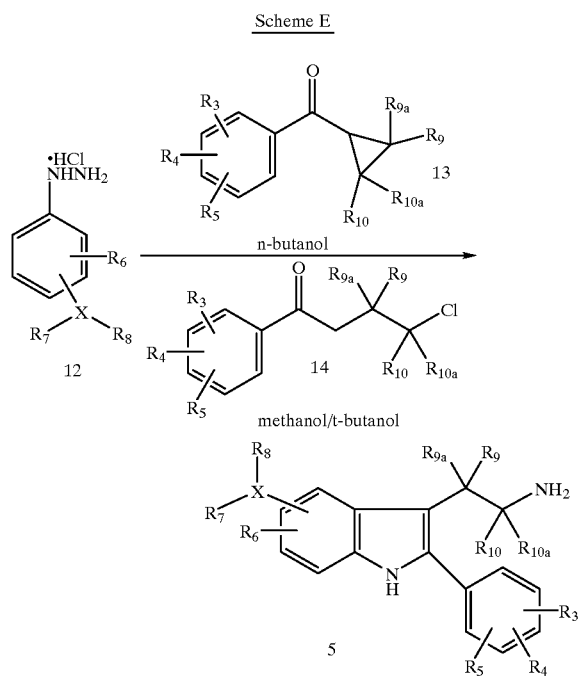

Reaction Scheme E

As shown in reaction Scheme E treatment of an arylhydrazine or arylhydrazine hydrochloride (12) with an arylcyclopropylketone of type (13) in a polar organic solvent such as methanol, ethanol, n-propanol, isopropanol, n-butanol, t-butanol, preferably n-butanol, at a temperature of 70°–120° C. for a period of 8–24 hours gives 2-aryltryptamine (5). Alternatively, when an arylhydrazine or arylhydrazine hydrochloride (12) is treated with an arylbutyl ketone of type (14) containing a leaving group (chloride, bromide, iodide, O-methansulfonate, O-trifluoromethansulfonate, or the like) at the 4-position in a polar solvent such as methanol, ethanol, n-propanol, isopropanol, n-butanol, t-butanol, or mixtures thereof at room temperature for a period of 30 minutes to 2 hours followed by heating to a temperature of 65°–100° C. for 4–24 hours, 2-aryltryptamine (5) is produced.

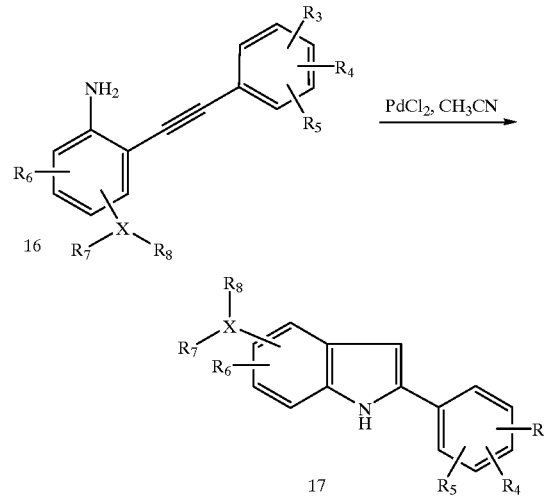

Reaction Scheme F

As shown in reaction Scheme F iodoanilines of type (15) may be reacted with aryl acetylenes, an appropriate palladium (O) catalyst such as tetrakis(triphenylphosphine) palladium, a copper (I) halide such as cuprous bromide in an inert organic solvent such as triethylamine at a temperature of 50°–88° C. for a period of 30 minutes to 5 hours to provide the diarylacetylene (16). Acetylene (16) may be further modified by treatment with a palladium (II) catalyst such as palladium (II) chloride or palladium (II) acetate in an inert organic solvent such as acetonitrile at a temperature of 50°–82° C. for a period of 30 minutes to 6 hours to give 2-arylindole (17).

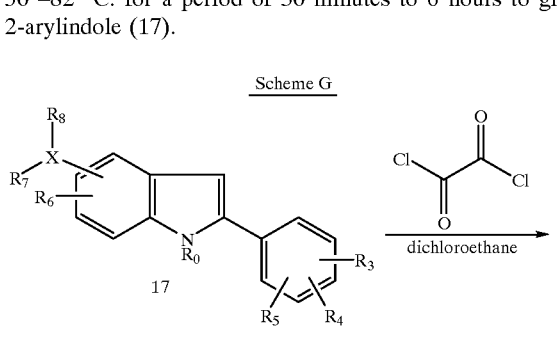

-continued

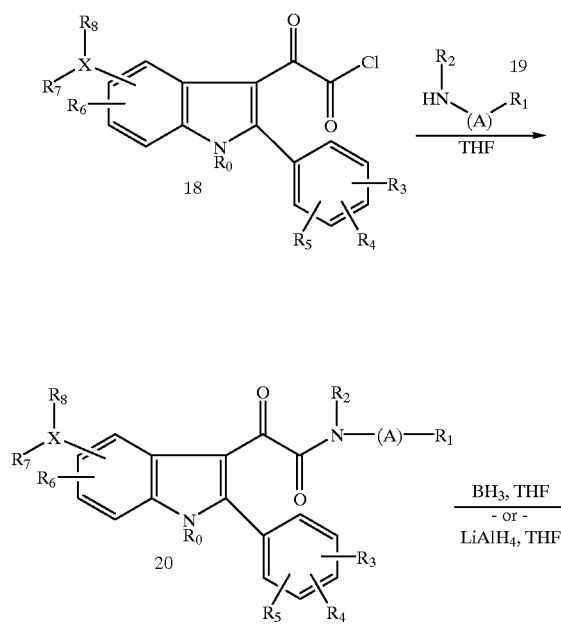

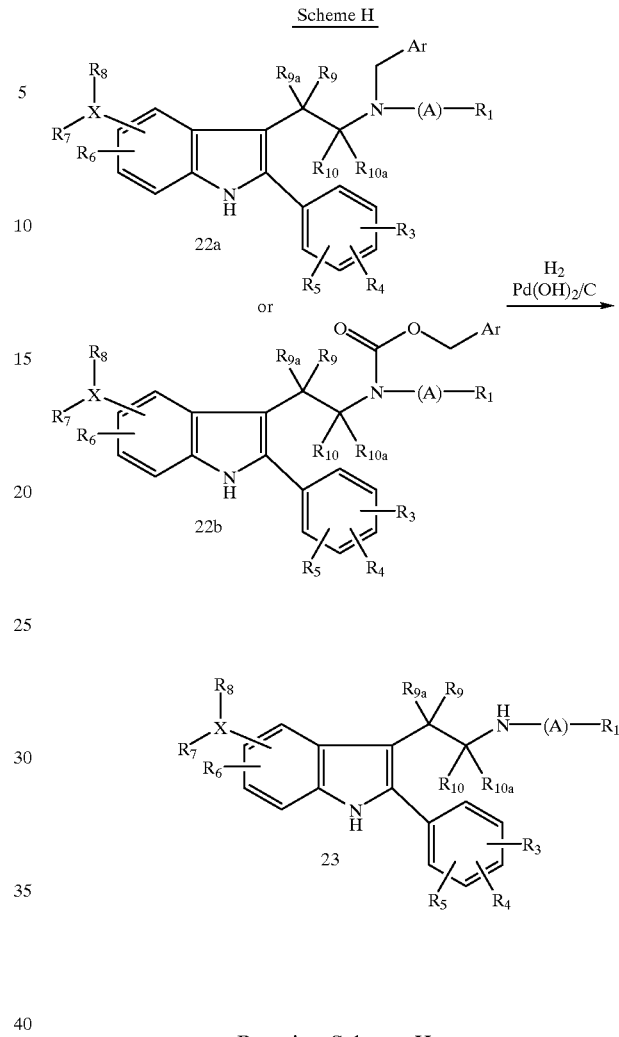

Reaction Scheme G

As shown in reaction Scheme G, treatment of 2-arylindole (17) with oxalyl chloride neat or in an inert organic solvent such as methylene chloride, chloroform, dichloroethane, tetrahydrofuran or the like at a temperature of 25°–65° C. for a period of 3–24 hours gives the acylchloride adduct (18). The crude product (18) may be reacted with an amine of type (19) in an inert organic solvent such as diethylether, tetrahydrofuran, methylene chloride, chloroform or the like and an amine base such as triethylamine, diisopropylethylamine or pyridine at a temperature of 0° C.–25° C. for a period of 30 minutes to 4 hours to provide the amide derivative (20). Amide (20) may be further modified by treatment with a reducing agent such as borane or lithium aluminum hydride in an inert organic solvent such as tetrahydrofuran at elevated temperatures, preferably reflux, for a period of 1–5 hours to give compound (21).

Reaction Scheme H

As shown in reaction Scheme H, N-benzyl derivatives of type (22a) or N-benzyloxycarbonyl derivatives of type (22b) may be reduced to provide the secondary amine analogs (7) by treatment with hydrogen (1 atm) and an appropriate catalyst such as palladium on carbon, palladium hydroxide on carbon, or the like in an inert organic solvent such as tetrahydrofuran, ethyl acetate, methanol, ethanol, or mixtures thereof to which has been added a weak acid such as 30% aqueous acetic acid for a period of 10 minutes to 3 hours or until the aryl group has been removed to give the secondary amine

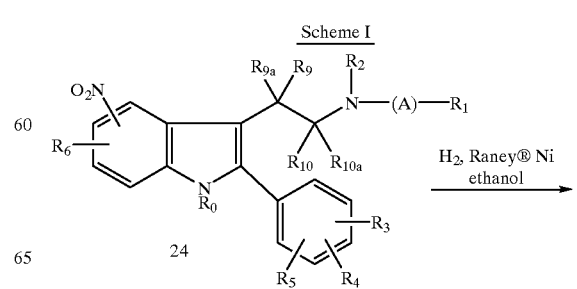

-continued

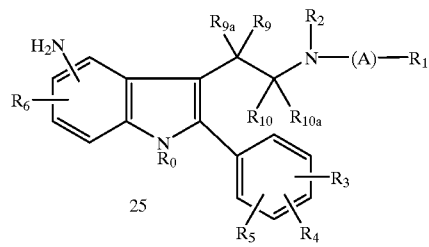

25

Reaction Scheme I

As shown in reaction Scheme I, treatment of a nitroindole of type (24) with hydrogen (1 atm) and an appropriate catalyst such as Raney® Nickel in an inert organic solvent such as ethanol, methanol, or the like at room temperature for a period of 2–12 hours gives the corresponding aminoindole derivative (25).

Scheme J

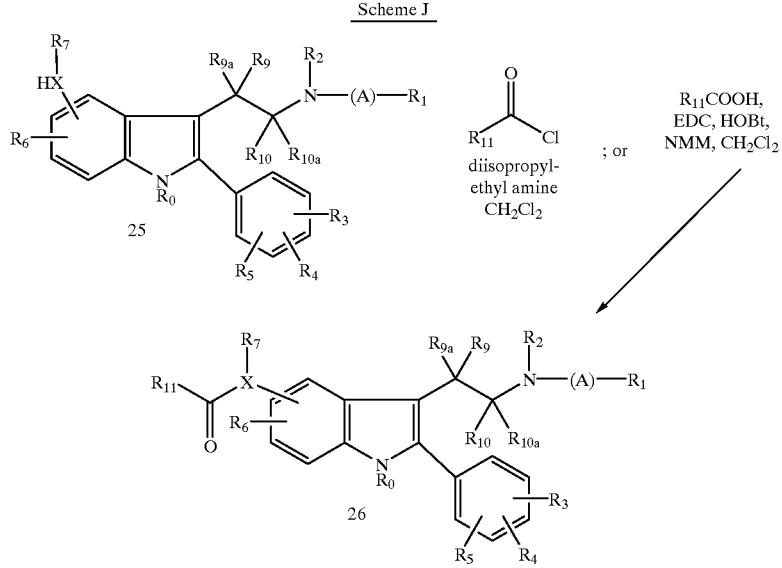

Reaction Scheme J

As shown in reaction Scheme J. amino- or hydroxyindole (25) may be modified by acylation under a variety of conditions. For example, treatment of (25) with an acid chloride, acid anhydride or active ester and an amine base such as triethylamine, diisopropylethylamine, pyridine, or the like in an inert organic solvent such as methylene chloride, chloroform, tetrahydrofuran, or mixtures thereof at 0° C. to room temperature for a period of 1 to 12 hours gives the corresponding amide or ester derivatives (26). Alternatively (25) may be coupled with a carboxylic acid by one of the many dehydrating agents commonly employed. For instance, treatment of aminoindole (25) with an appropriate carboxylic acid and 1-(3-dimethylaminopropyl)-3-ethylcarbodiimide hydrochloride (EDC), 1,3-dicyclohexylcarbodiimide (DCC) or the like with or without 1-hydroxybenzotriazole (HOBt) and a tertiary amine base such as N-methylmorpholine (NMM), triethylamine or the like in an inert organic solvent such as methylene chloride, chloroform, dimethylformamide, or mixtures thereof at or near room temperature for a period of 3–24 hours provides the corresponding amide or ester derivative (26).

Scheme K

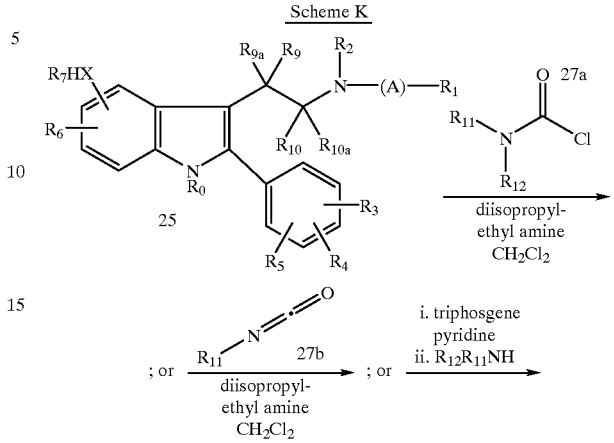

-continued

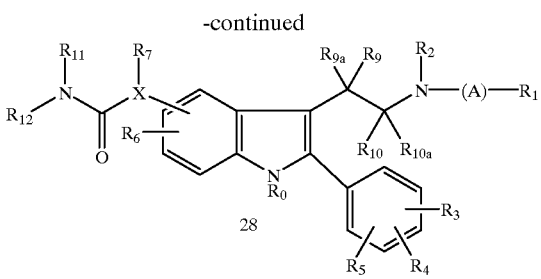

Reaction Scheme K

As shown in reaction Scheme K, urea or carbamate derivatives of (25) can be prepared by treatment with a carbamoyl chloride of type (27a), or alternatively with an isocyanate reagent of type (27b), and an amine base such as pyridine, triethylamine, diisopropylethylamine, N-methylmorpholine or the like in an inert organic solvent such as methylene chloride, chloroform, dimethylformamide, tetrahydrofuran or mixtures thereof at a temperature of 0°–65° C. for a period of 1–72 hours to give (28). Compound (25) can also be modified by treatment with a bis(electrophilic) reagent such as phosgene, triphosgene, 1,1'-carbonyldiimidazole, N,N'-disuccinimidyl carbonate, or the like with or without the addition of an amine base such as pyridine, triethylamine, diisopropylethylamine, N-methylmorpholine in an inert solvent such as methylene chloride, chloroform, or the like at a temperature of −20°–0° C. for a period of 20 minutes to 2 hours. After this time, the reaction mixture is treated with an appropriate mono- or disubstituted amine at −20°–25° C. for a period of 1–5 hours to give the urea or carbamate analog (28).

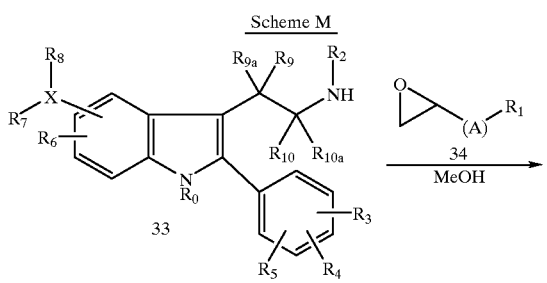

Reaction Scheme L

As shown in reaction Scheme L, amine (25) can be modified by treatment with an appropriate sulfonyl chloride of type (29) or sulfamyl chloride of type (30) with an amine base such as pyridine, triethylamine, diisopropylethylamine, N-methylmorpholine in an inert solvent such as methylene chloride, chloroform, dichloroethane or the like at a temperature of −20°–25° C. for a period of 20 minutes to 2 hours to give the corresponding N-sulfonamide (31) or N-sulfamylamide (32) derivatives, respectively.

Reaction Scheme M

As shown in reaction Scheme M, the 2-aryltryptamine (33) can be modified by treatment with an epoxide such as

(34) in an inert organic solvent such as methanol, ethanol, isopropanol, butanol, tert-butanol, or mixtures thereof at a temperature of 65°–110° C. for a period of 8–20 hours to give the corresponding amino-alcohol derivative (35).

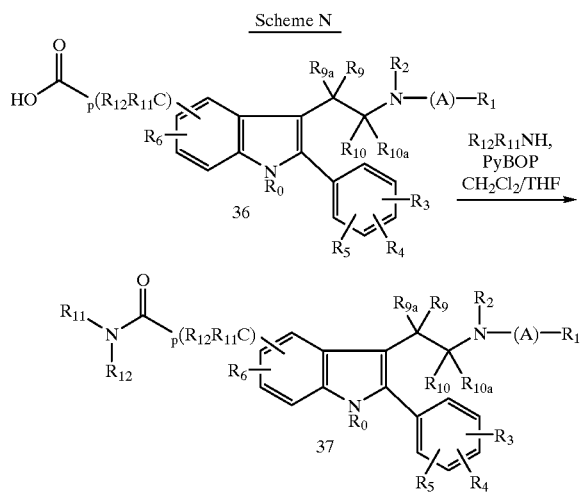

Reaction Scheme N

As shown in reaction Scheme N, amide derivatives of an an acid-containing indole derivative such as (36) can be prepared by treatment with an appropriate amine ($R_{12}R_{11}$NH) and a suitable coupling agent such as benzotriazol-1-yloxy-tris(pyrrolidino)phosphonium hexafluorophosphate (PyBOP), benzotriazol-1-yloxy-tris(dimethylamino) phosphonium hexafluorophosphate (BOP), 1-(3-dimethylaminopropyl)-3-ethylcarbodiimide hydrochloride (EDC), 1,3-dicyclohexylcarbodiimide (DCC) or the like with or without 1-hydroxybenzotriazole (HOBt) and a tertiary amine base such as N-methylmorpholine (NMM), triethylamine or the like in an inert organic solvent such as methylene chloride, chloroform, tetrahydrofuran, dimethylformamide, or mixtures thereof at or near room temperature for a period of 3–24 hours provides the corresponding amide derivative (37).

The compounds of the present invention are useful in the treatment of various sex-hormone related conditions in men and women. This utility is manifested in their ability to act as antagonists of the neuropeptide hormone GnRH as demonstrated by activity in the following in vitro assays.

Rat pituitary GnRH receptor binding assay:

Crude plasma membranes prepared from rat pituitary tissues were incubated in a Tris.HCl buffer (50 mM, PH. 7.5) containing bovine serum albumin (0.1%), [I-125]D-t-Bu-Ser6-Pro9-ethyl amide-GnRH, and the desired concentration of a test compound. The assay mixtures were incubated at 4° C. for 90–120 minutes followed by rapid filtration and repeated washings through a glass fiber filter. The radioactivity of membrane bound radioligands was determined in a gamma-counter. From this data, the $IC_{50}$ of the radioligand binding to GnRH receptors in the presence of test compound was estimated.

Inhibition of LH release assay:

Active compounds from the GnRH receptor binding assay were further evaluated with an in vitro LH release assay to confirm their antagonist activity (blocking GnRH-induced LH release).

1. Sample Preparation

The compounds to be assayed were dissolved and diluted in DMSO. The final concentration of DMSO in the incubation medium was 0.5%.

2. Assay

The Wistar male rats (150–200 grams) were obtained from Charles River Laboratories (Wilmington, Mass.). Rats were maintained at a constant temperature (25° C.) on a 12-hr light, 12-hr dark cycle. Rat chow and water were available ad libitum. The animals were sacrificed by decapitation and pituitary glands were aseptically removed and placed in Hank's Balanced Salt Solution (HBSS) in a 50-mL polypropylene centrifuge tube. The collection tube was centrifuged for 5 min at 250×g, and HBSS was removed by aspiration. Pituitary glands were transferred to a disposable petri plate and minced with a scalpel. The minced tissue was then transferred to a 50-mL disposable centrifuge tube by suspending the tissue fragments in three successive 10-mL aliquots of HBSS containing 0.2% collagenase and 0.2% hyaluronidase. The cell dispersion was carried out in a water bath at 37° C. with gentle stirring for 30 min. At the end of the incubation, the cells were aspirated 20 to 30 times with a pipet and the undigested pituitary fragments were allowed to settle for 3 to 5 min. The suspended cells were removed by aspiration, and then subjected to a 1200×g centrifugation for 5 min. The cells were then resuspended in Culture medium. The undigested pituitary fragments were treated with 30 mL aliquots of the digestion enzymes as above for a total of 3 digestions with the collagenase/hyaluronidase mixture. The resulting cell suspensions were pooled, counted and diluted to a concentration of 3×10⁵ cells/ml, and 1.0 ml of this suspension was placed in each well of a 24-well tray (Costar, Cambridge, Mass.). Cells were maintained in a humidified 5% $CO_2$–95% air atmosphere at 37° C. for 3 to 4 days. The culture medium consisted of DMEM containing 0.37% $NaHCO_3$, 10% horse serum, 2.5% fetal bovine serum, 1% non-essential amino acids, 1% glutamine, and 0.1 % gentamycin. On the day of an experiment, cells were washed three times 1½ hrs prior to and two more times immediately before the start of the experiment with DMEM containing 0.37% $NaHCO_3$, 10% horse serum, 2.5% fetal bovine serum, 1% non-essential amino acids(100×), 1% glutamine(100×), 1% Penicillin/Streptomycin(10,000 Units of Penicillin and 10,000 micrograms of Streptomycin per ml), and 25 mM HEPES, pH 7.4. LH release was initiated by adding 1 ml of fresh medium containing test compounds in the presence of 2 nM GnRH to each well in duplicate. Incubation was carried out at 37° C. for 3 hr. After incubation, medium was removed and centrifuged at 2,000×g for 15 min to remove any cellular material. The supernatant fluid was removed and assayed for LH content with a double antibody RIA procedure using materials obtained from Dr. A. F. Parlow (Harbor-UCLA Medical Center, Torrance, Calif.).

The compounds of formula I are useful in a number of areas affected by GnRH. They may be useful in sex-hormone related conditions, sex-hormone dependent cancers, benign prostatic hypertrophy or myoma of the uterus. Sex-hormone dependent cancers which may benefit from the administration of the compounds of this invention include prostatic cancer, uterine cancer, breast cancer and pituitary gonadotrophe adenomas. Other sex-hormone dependent conditions which may benefit from the administration of the compounds of this invention include endometriosis, polycystic ovarian disease, uterine fibroids and precocious puberty. The compounds may also be used in combination with an angiotensin-converting enzyme inhibitor such as Enalapril or Captopril, an angiotensin II-receptor antagonist such as Losartan or a renin inhibitor for the treatment of uterine fibroids.

The compounds of the invention may also be useful for controlling pregnancy, as a contraceptive in both men and women, for in vitro fertilization, in the treatment of premenstrual syndrome, in the treatment of lupus erythematosis, in the treatment of hirsutism, in the treatment of irritable bowel syndrome and for the treatment of sleep disorders such as sleep apnea.

A further use of the compounds of this invention is as an adjunct to growth hormone therapy in growth hormone deficient children. The compounds may be administered with growth hormone or a compound which increases the endogenous production or release of growth hormone. Certain compounds have been developed which stimulate the release of endogenous growth hormone. Peptides which are known to stimulate the release of endogenous growth hormone include growth hormone releasing hormone, the growth hormone releasing peptides GHRP6 and GHRP-1 (described in U.S. Pat. No. 4,411,890, PCT Patent Pub. No. WO 89/07110, and PCT Patent Pub. No. WO 89/071 11) and GHRP-2 (described in PCT Patent Pub. No. WO 93/04081), as well as hexarelin (*J. Endocrinol Invest.*, 15(Suppl 4), 45 (1992)). Other compounds which stimulate the release of endogenous growth hormone are disclosed, for example, in the following: U.S. Pat. Nos. 3,239,345; 4,036,979; 4,411,890; 5,206,235; 5,283,241; 5,284,841; 5,310,737; 5,317,017; 5,374,721; 5,430,144; 5,434,261; 5,438,136; EPO Patent Pub. No. 0,144,230; EPO Patent Pub. No. 0,513,974; PCT Patent Pub. No. WO 94/07486; PCT Patent Pub. No. WO 94/08583; PCT Patent Pub. No. WO 94/11012; PCT Patent Pub. No. WO 94/13696; PCT Patent Pub. No. WO 94/19367; PCT Patent Pub. No. WO 95/03289; PCT Patent Pub. No. WO 95/03290; PCT Patent Pub. No. WO 95/09633; PCT Patent Pub. No. WO 95/11029; PCT Patent Pub. No. WO 95/12598; PCT Patent Pub. No. WO 95/13069; PCT Patent Pub. No. WO 95/14666; PCT Patent Pub. No. WO 95/16675; PCT Patent Pub. No. WO 95/16692; PCT Patent Pub. No. WO 95/17422; PCT Patent Pub. No. WO 95/17423; *Science*, 260, 1640–1643 (Jun. 11, 1993); *Ann. Rep. Med. Chem.*, 28, 177–186 (1993); *Bioorg. Med. Chem. Ltrs.*, 4(22), 2709–2714 (1994); and *Proc. Natl. Acad. Sci. USA* 92, 7001–7005 (July 1995).

Representative preferred growth hormone secretagoues employed in the present combination include the following:

1) N-[1(R)-[(1,2-Dihydro-1-methanesulfonylspiro[3H-indole-3,4'-piperidin]-1'-yl)carbonyl]-2-(1H-indol-3-yl)ethyl]-2-amino-2-methylpropanamide;
2) N-[1(R)-[(1,2-Dihydro-1-methanecarbonylspiro[3H-indole-3,4'-piperidin]-1'-yl)carbonyl]-2-(1H-indol-3-yl)ethyl]-2-amino-2-methylpropanamide;
3) N-[1(R)-[(1,2-Dihydro-1-benzenesulfonylspiro[3H-indole-3,4'-piperidin]-1'-yl)carbonyl]-2-(1H-indol-3-yl)ethyl]-2-amino-2-methylpropanamide;
4) N-[1(R)-[(3,4-Dihydro-spiro[2H-1-benzopyran-2,4'-piperidin]-1'-yl) carbonyl]-2-(1 H-indol-3-yl)ethyl]-2-amino-2-methylpropanamide;
5) N-[1(R)-[(2-Acetyl-1,2,3,4-tetrahydrospiro[isoquinolin-4,4'-piperidin]-1'-yl)carbonyl]-2-(indol-3-yl)ethyl]-2-amino-2-methylpropanamide;
6) N-[1(R)-[(1,2-Dihydro-1-methanesulfonylspiro[3H-indole-3,4'-piperidin]-1'-yl)carbonyl]-2-(phenylmethyloxy)ethyl]-2-amino-2-methylpropanamide;
7) N-[1(R)-[(1,2-Dihydro-1-methanesulfonylspiro[3H-indole-3,4'-piperidin]-1'-yl)carbonyl]-2-(phenylmethyloxy)ethyl]-2-amino-2-methylpropanamide methanesulfonate;
8) N-[1(R)-[(1,2-Dihydro-1-methanesulfonylspiro[3H-indole-3,4'-piperidin]-1'-yl)carbonyl]-2-(2',6'-difluorophenylmethyloxy)ethyl]-2-amino-2-methylpropanamide;
9) N-[1(R)-[(1,2-Dihydro-1-methanesulfonyl-5-fluorospiro[3H-indole-3,4'-piperidin)-1'-yl)carbonyl]-2-(phenylmethyloxy)ethyl]-2-amino-2-methylpropanamide;
10) N-[1(S)-[(1,2-Dihydro-1-methanesulfonylspiro[3H-indole-3,4'-piperidin]-1'-yl) carbonyl]-2-(phenylmethylthio)ethyl]-2-amino-2-methylpropanamide;
11) N-[(R)-[(1,2-Dihydro-1-methanesulfonylspiro[3H-indole-3,4'-piperidin]-1'-yl)carbonyl]-3-phenylpropyl]-2-amino-2-methylpropanamide;
12) N-[1(R)-[(1,2-Dihydro-1-methanesulfonylspiro[3H-indole-3,4'-piperidin]-1'-yl)carbonyl]-3-cyclohexylpropyl]-2-amino-2-methylpropanamide;
13) N-[1(R)-[(1,2-Dihydro-1-methanesulfonylspiro[3H-indole-3,4'-piperidin]-1'-yl)carbonyl]-4-phenylbutyl]-2-amino-2-methylpropanamide;
14) N-[(R)-[(1,2-Dihydro-1-methanesulfonylspiro[3H-indole-3,4'-piperidin]-1'-yl)carbonyl]-2-(5-fluoro-1H-indol-3-yl)ethyl]-2-amino-2-methylpropanamide;
15) N-[1(R)-[(1,2-Dihydro-1-methanesulfonyl-5-fluorospiro[3H-indole-3,4'-piperidin]-1'-yl)carbonyl]-2-(5-fluoro-1H-indol-3-yl)ethyl]-2-amino-2-methylpropanamide;
16) N-[1(R)-[(1,2-Dihydro-1-(2-ethoxycarbonyl)methylsulfonylspiro-[3H-indole-3,4'-piperidin]-1'-yl) carbonyl]-2-(1H-indol-3-yl)ethyl]-2-amino-2-methylpropanamide;
17) N-[1(R)-[(1,2-Dihydro-1,1-dioxospiro[3H-benzothiophene-3,4'-piperidin]-1'-yl)carbonyl]-2-(phenylmethyloxy)ethyl]-2-amino-2-methylpropanamide;

and pharmaceutically acceptable salts thereof.

The compounds of the invention may also be used in combination with bisphosphonates (bisphosphonic acids) and other agents, such as growth hormone secretagogues, e.g. MK-0677, for the treatment and the prevention of disturbances of calcium, phosphate and bone metabolism, in particular, for the prevention of bone loss during therapy with the GnRH antagonist, and in combination with estrogens, progesterones and or androgens for the prevention or treatment of bone loss or hypogonadal symptoms such as hot flashes during therapy with the GnRH antagonist.

Bisphosphonates (bisphosphonic acids) are known to inhibit bone resorption and are useful for the treatment of bone lithiasis as disclosed in U.S. Pat. No. 4,621,077 to Rosini, et al.

The literature discloses a variety of bisphosphonic acids which are useful in the treatment and prevention of diseases involving bone resorption. Representative examples may be found in the following: U.S. Pat. Nos. 3,251,907; 3,422,137; 3,584,125; 3,940,436; 3,944,599; 3,962,432; 4,054,598; 4,267,108; 4,327,039; 4,407,761; 4,578,376; 4,621,077; 4,624,947; 4,746,654; 4,761,406; 4,922,007; 4,942,157; 5,227,506; 5,270,365; EPO Patent Pub. No. 0,252,504; and *J. Org. Chem.*, 36, 3843 (1971).

The preparation of bisphosphonic acids and halobisphosphonic acids is well known in the art. Representative examples may be found in the above mentioned references which disclose the compounds as being useful for the treatment of disturbances of calcium or phosphate metabolism, in particular, as inhibitors of bone resorption.

Preferred bisphosphonates are selected from the group of the following compounds: alendronic acid, etidrononic acid, clodronic acid, pamidronic acid, tiludronic acid, risedronic acid, 6-amino-1-hydroxy-hexylidene-bisphosphonic acid, and 1-hydroxy-3(methylpentylamino)-propylidene-bisphosphonic acid; or any pharmaceutically acceptable salt thereof. A particularly preferred bisphosphonate is alendronic acid (alendronate), or a pharmaceutically acceptable salt thereof. An especially preferred bisphosphonate is alendronate sodium, including alendronate sodium trihydrate. Alendronate sodium has received regulatory approval for marketing in the United States under the trademark FOSAMAX®.

Additionally, a compound of the present invention may be co-administered with a 5α-reductase 2 inhibitor, such as finasteride or epristeride; a 5α-reductase 1 inhibitor such as 4,7β-dimethyl-4-aza-5α-cholestan-3-one, 3-oxo-4-aza-4,7β-dimethyl- 16β-(4-chlorophenoxy)-5α-androstane, and 3-oxo-4-aza-4,7β-dimethyl-16β-(phenoxy)-5α-androstane as disclosed in WO 93/23420 and WO 95/11254; dual inhibitors of 5α-reductase 1 and 5α-reductase 2 such as 3-oxo-4-aza-17β-(2,5-trifluoromethylphenyl-carbamoyl)-5α-androstane as disclosed in WO 95/07927; antiandrogens such as flutamide, casodex and cyproterone acetate, and alpha-1 blockers such as prazosin, terazosin, doxazosin, tamsulosin, and alfuzosin.

Further, a compound of the present invention may be used in combination with growth hormone, growth hormone releasing hormone or growth hormone secretagogues, to delay puberty in growth hormone deficient children, which will allow them to continue to gain height before fusion of the epiphyses and cessation of growth at puberty.

For combination treatment with more than one active agent, where the active agents are in separate dosage formulations, the active agents may be administered separately or in conjunction. In addition, the administration of one element may be prior to, concurrent to, or subsequent to the administration of the other agent.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy beans, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter, arrest or reverse the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. Preferably, doses of the compound of structural formula I useful in the method of the present invention range from 0.01 to 1000 mg per adult human per day. Most preferably, dosages range from 0.1 to 500 mg/day. For oral administration, the compositions are preferably provided in the form of tablets containing 0.01 to 1000 milligrams of the active ingredient, particularly 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. An effective amount of the drug is ordinarily supplied at a dosage level of from about 0.0002 mg/kg to about 50 mg/kg of body weight per day. The range is more particularly from about 0.001 mg/kg to 1 mg/kg of body weight per day.

Advantageously, the active agent of the present invention may be administered in a single daily dose, or the total daily dosage may be administered in dividend doses of two, three or four times daily.

The amount of active ingredient that may be combined with the carrier materials to produce a single dosage form will vary depending upon the host treated and the particular mode of administration.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The following examples illustrate the preparation of some of the compounds of the invention and are not to be construed as limiting the invention disclosed herein.

EXAMPLE 1

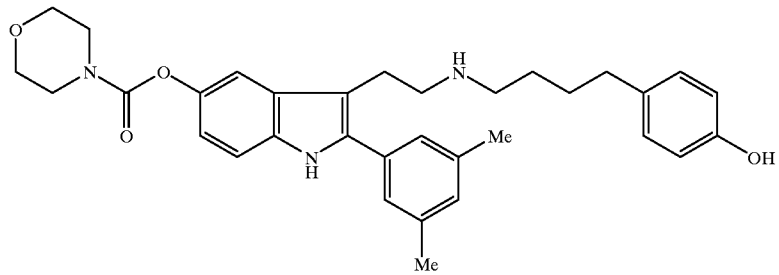

Morpholine-4carboxylic acid 2-(3,5-dimethylphenyl)-3-[2-[4-(4-hydroxyphenyl) butylamino]ethyl]-1H-indol-5-yl ester Step 1A 2-[2-(5-benzyloxy-1H-indol-3-yl)ethyl] isoindole-1,3-dione To a stirred suspension of 5-benzyloxytryptamine hydrochloride (1.0 g in 10 mL of dry tetrahydrofuran) was added triethylamine (0.50 mL) followed by N-carbethoxyphthalimide (750 mg) and the mixture heated to reflux on an oil bath. After 48 hours the reaction was cooled to room temperature, filtered and the filtrate concentrated in vacuo. The resulting solid was suspended in a mixture of hexane/methylene chloride (2.5:1, 50 mL) and filtered to give the title compound (1.3 g).

Step 1B 2-[2-(5-benzyloxy-2-bromo-1H-indol-3-yl)ethyl] isoindole-1,3-dione

To a solution of 2-[2-(5-benzyloxy-1H-indol-3-yl)ethyl] isoindole-1,3-dione (800 mg in a mixture of dry 25 mL tetrahydrofuran and 25 mL dry chloroform) at 0° C. was added pyridinium hydrobromide perbromide (666 mg) and the mixture stirred at 0° C. After 23 minutes the reaction was quenched by the addition of saturated sodium bicarbonate and extracted with ethyl acetate. The organic portion was washed with saturated sodium bicarbonate (3×) and 0.3M sodium bisulfate (3×) then dried over magnesium sulfate. Purification of the concentrate by flash chromatography on silica gel (hexane:ethyl acetate, 7:2) followed by repurification by flash chromatography on silica gel (methylene chloride) gave the title compound (632 mg).

Step 1C 2-[2-[5-benzyloxy-2-(3,5-dimethylphenyl)-1H-indol-3-yl]ethyl]isoindole-1,3-dione To a solution of 2-[2-(5-benzyloxy-2-bromo-1H-indol-3-yl)ethyl]isoindole-1,3-dione (500 mg in a mixture of 6 mL ethanol and 16 mL toluene) was added 3,5-dimethylphenyl boronic acid (205 mg) followed by 2.7 mL of 1M sodium carbonate. To the stirred solution was added lithium chloride (156 mg) followed by tetrakis(triphenylphosphine) palladium (78 mg) and the mixture heated to reflux on an oil bath. After 2 hours the mixture was cooled to room temperature and concentrated in vacuo. Purification by flash chromatography on silica gel (hexane:methylene chloride:ethyl acetate, 15:8:1 then 12:8:1) gave the title compound (479 mg).

Step 1D 2-[2-[2-(3,5-dimethylphenyl)-5-hydroxy-1H-indol-3-yl]ethyl]isoindole-1,3-dione To a stirred solution of 2-[2-[5-benzyloxy-2-(3,5-dimethylphenyl)-1H-indol-3-yl]ethyl]isoindole-1,3-dione (510 mg in 20 mL dry ethyl acetate was added 197 mg of 10% palladium on carbon catalyst. The reaction flask was fitted with a hydrogen balloon, evacuated and recharged with hydrogen (3 times) and stirred at room temperature. After 37 hours the reaction was flushed with nitrogen, filtered over diatomaceous earth and concentrated in vacuo to provide the title compound (418 mg).

Step 1E 3-(2-aminoethyl)-2-(3,5-dimethylphenyl)-1H-indol-5-ol

To a solution of 2-[2-[2-(3,5-dimethylphenyl)-5-hydroxy-1H-indol-3-yl]ethyl]isoindole-1,3-dione (418 mg in a mixture of 7 mL ethanol and 7 mL tetrahydrofuran) was added 2.5 mL of 95% aqueous hydrazine and the reaction stirred at room temperature. After 12 hours the mixture was concentrated in vacuo and purified by flash chromatography on silica gel (methylene chloride:methanol:ammonium hydroxide, 89:11:1) to provide the title compound (228 mg).

Step 1F 4-(4-benzyloxyphenyl-N-{2-[2-(3,5-dimethylphenyl)-5-hydroxy-1H-indol-3-yl]ethyl]butyramide To a stirred solution of 4-benzyloxyphenylbutyric acid (159 mg in a mixture of 2 mL methylene chloride and 0.5 mL N,N-dimethylformamide) was added 1-hydroxybenzotriazole (110 mg) and 1-(3-dimethylaminopropyl)-3-ethylcarbodiimide hydrochloride (113 mg) and the reagents allowed to mix for 30 minutes. At this time a solution of 3-(2-aminoethyl)-2-(3,5-dimethylphenyl)-1H-indol-5-ol (144 mg in 4 mL N,N-dimethylformamide) was added and the reaction stirred at room temperature. After 6 hours, the mixture was concentrated in vacuo and purified by flash chromatography on silica gel (hexane:ethyl acetate, 4:5) to give the title compound (241 mg).

Step 1G 3-[2-[4-(4-benzyloxyphenyl)butylamino]ethyl]-2-(3,5-dimethylphenyl)-1H-indol-5-ol To a stirred solution of 4-(4-benzyloxyphenyl)-N-{2-[2-(3,5-dimethylphenyl)-5-hydroxy-1H-indol-3-yl]ethyl}butyramide (241 mg in 10 mL dry tetrahydrofuran) was added 4 mL of a 1M solution of borane in tetrahydrofuran and the mixture heated slowly to reflux on an oil bath. After 2 hours the mixture was cooled to room temperature and the excess borane quenched by the careful addition of methanol. The mixture was concentrated to half-volume, treated with N,N-dimethylethanolamine (1.4 mL) and heated to reflux on an oil bath. After 3 hours the mixture was cooled to room temperature and concentrated in vacuo. Purification by flash chromatography on silica gel (methylene chloride:methanol, 92:8) gave the title compound (234 mg).

Step 1H [4-(4-benzyloxyphenyl)-butyl]-[2-[2-(3,5-dimethylphenyl)-5-hydroxy-1H-indol-3yl]ethyl]carbamic acid benzyl ester To a solution of 3-[2-[4-(4-benzyloxyphenyl)butylamino]ethyl]-2-(3,5-dimethylphenyl)-1H-indol-5-ol (234 mg in 5 mL of dry methylene chloride) at −78° C. was added benzyl chloroformate (0.082 mL) and diisopropylethylamine (0.104 mL) and the mixture stirred at room temperature. After 1 hour the reaction was quenched by the addition of saturated sodium bicarbonate and extracted with ethyl acetate. The organic portion was washed with saturated ammonium chloride, dried over magnesium sulfate and concentrated in vacuo. Purification by flash chromatography on silica gel (hexane:ethyl acetate, 3:1 then 2:1) gave the title compound (155 mg).

Step 1I Morpholine-4-carboxylic acid 3-(2-[benzyloxycarbonyl-[4-(4- benzyoxy-phenyl)butyl]amino]-ethyl)-2-(3,5-dimethylphenyl)-1H-indol-5-yl ester To a stirred solution of 2-(3,5-dimethylphenyl)-5-hydroxy-N-(4-benzyloxyphenylbutyl)-N-(benzyloxycarbonyl)tryptamine [4-(4-benzyloxyphenyl)-butyl]-[2-[2-(3,5-dimethylphenyl)-5-hydroxy-1H-indol-3-yl]ethyl]carbamic acid benzyl ester (20 mg in 2 mL dry methylene chloride) at 0° C. was added triphosgene (4.8 mg) and pyridine (0.040 mL of a 10% solution in methylene chloride) and the reagents allowed to mix for 20 minutes. This was than added by cannula to a solution of morpholine (0.10 mL in 1 mL dry methylene chloride) at 0° C. followed by warming to room temperature. After 45 minutes, the reaction was quenched by the addition of 0.3M sodium bisulfate and extracted with ethyl acetate. The organic portion was washed with 0.3M sodium bisulfate (3×) and brine, then dried over magnesium sulfate and concentrated in vacuo. Purification by flash chromatography on silica gel hexane:ethyl acetate, 3:2) gave the title compound (20 mg).

Step 1J Morpholine-4-carboxylic acid 2-(3,5-dimethylphenyl)-3-[2-[4-(4-hydroxy-phenyl)butylamino]ethyl]-1H-indol-5yl ester To a stirred solution of morpholine-4-carboxylic acid 3-(2-[benzyloxycarbonyl-[4-(4-benzyloxy-phenyl)butyl]amino]-ethyl)-2-(3,5-dimethylphenyl)-1H-indol-5-yl ester (20 mg in a mixture of 2 mL tetrahydrofuran and 0.5 mL methanol) was added 16.8 mg of 10% palladium on carbon catalyst followed by acetic acid (0.010 mL of a 30% solution in water). The reaction flask was fitted with a hydrogen balloon, evacuated and recharged with hydrogen (3 times) and stirred at room temperature. After 1.5 hours the reaction was flushed with nitrogen, filtered over diatomaceous earth and concentrated in vacuo. Purification by flash chromatography (methylene chloride:methanol:ammonium hydroxide, 90:7:1) gave the title compound (12 mg). m/e=542 (M+H)

PREPARATION OF SYNTHETIC INTERMEDIATES

4-(4-benzyloxyphenyl)butyric acid

Step A: 4-(4-Benzyloxyphenyl)butyric acid benzyl ester

To a stirred solution of 4-hydroxyphenylbutyric acid (810 mg in 8 mL N,N-dimethylformamide) at 0° C. was added sodium hydride (290 mg of an 80% dispersion in mineral oil) and the mixture allowed to warm to room temperature. Benzyl bromide (1.2 mL) was added after 20 minutes and the mixture stirred at room temperature. After 13 hours the reaction was quenched by the addition of saturated ammonium chloride and extracted with ethyl acetate. The organic portion was washed with water (4×), dried over sodium sulfate and concentrated in vacuo. Purification by flash chromatography on silica gel (hexane:ethyl acetate, 13:1) gave the title compound (1.45 g)

Step B: 4-(4-Benzyloxyphenyl)butyric acid

To a stirred solution of 4-(4-benzyloxyphenyl)butyric acid benzyl ester (277 mg in a mixture of 3 mL methanol and 1 mL methylene chloride) at 0° C. was added 1.5 mL of 5M sodium hydroxide and the mixture warmed to room temperature. After 2 hours the mixture was acidified to pH 2 by the addition of aqueous hydrochloric acid, the aqueous portion extracted with ethyl acetate (5×) and the resulting organics concentrated in vacuo. Purification by flash chromatography on silica gel (methylene chloride:methanol, 94:6 then 96:4+0.25% TFA) gave the title compound (196 mg).

3,5-dimethylphenylboronic acid

To a solution of 5-bromo-m-xylene (1.5 g in 15 mL of dry tetrahydrofuran) at −78° C. was added 6.4 mL of a 1.4M solution of butyllithium in hexane and the mixture stirred for 20 minutes. At this time triisopropyl borate (2.8 mL) was added and the mixture allowed to warm to room temperature. After 1.5 hours the reaction was concentrated in vacuo to ⅓ volume then cooled to 0° C. and treated with 2N hydrochloric acid (9 mL) followed by warming to room temperature. After 4 hours the mixture was made basic by the addition of 2.5M sodium hydroxide and partitioned between ethyl ether (75 mL) and 1.25M sodium hydroxide. The organic layer was extracted with 1.25M sodium hydroxide (2×) and the aqueous portion then cooled to 0° C. and acidified to pH 3 by the dropwise addition of conc. hydrochloric acid. The white slurry was dissolved in methylene chloride, the organic portion dried over magnesium sulfate and concentrated in vacuo to provide the title compound (960 mg).

Following a procedure similar to that described above, the following compounds were prepared:

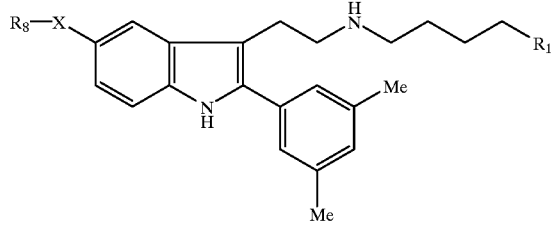

| Example | $R_1$ | X-$R_8$ | m/e |
|---|---|---|---|
| 1A | Ph-4-OH | O—CO-1-Piperazine | 541 (M + H) |
| 1B | Ph-4-OH | O—CO-Piperazine-CO—Me | 583 (M + H) |
| 1C | Ph-4-OH | O—CO—NH-4-Pyridine | 549 (M + H) |
| 1D | Ph-4-OH | O—CO-1-Piperidine | 540 (M + H) |
| 1E | Ph-4-OH | O—CO—NH-3-Pyridine | 549 (M + H) |
| 1F | Ph-4-OH | O—CO-Piperazine-$SO_2$—Me | 619 (M + H) |
| 1G | Ph-4-OH | O—CO-Piperazine-Me | 555 (M + H) |
| 1H | Ph-4-OH | O—CO-Piperazine-$CH_2$—CO—$NH_2$ | 598 (M + H) |
| 1I | Ph-4-OH | O—CO—NH-2-Pyridine | 549 (M + H) |
| 1J | Ph-4-OH | O—CO-Piperazine-CO—Et | 597 (M + H) |
| 1K | Ph-4-OH | O—CO-Piperazine-CO—O—Et | 613 (M + H) |
| 1L | Ph-4-OH | O—CO-Piperazine-$SO_2$—Et | 633 (M + H) |
| 1M | Ph-4-OH | O—CO-Piperazine-$SO_2$—CH—$(CH_3)_2$ | 647 (M + H) |
| 1N | Ph-4-OH | O—CO-Piperazine-$SO_2$—Ph | 681 (M + H) |
| 1O | Ph-4-OH | O—CO-Piperazine-CO—Pr | 611 (M + H) |
| 1P | Ph-4-OH | O—CO-Piperazine-CO—CH—$(CH_3)_2$ | 611 (M + H) |
| 1Q | Ph-4-OH | O—CO-Piperazine-Ph | 617 (M + H) |
| 1R | Ph-4-OH | O—CO-Piperazine-$SO_2$—Pr | 647 (M + H) |
| 1S | Ph-4-OH | O—CO-Piperazine-$CH_2$—CO—OMe | 613 (M + H) |
| 1T | Ph-4-OH | O—CO-Piperazine-$CH_2$—COOH | 599 (M + H) |
| 1U | Ph-4-N—(Et)—$SO_2CH_3$ | O—CO-Piperazine-$SO_2$—Et | 738 (M + H) |
| 1V | Ph-4-OH | O—CO-Piperazine-CO—NH—Me | 598 (M + H) |
| 1W | Ph-4-OH | O—CO-Piperazine-CO—NH—Et | 612 (M + H) |

-continued

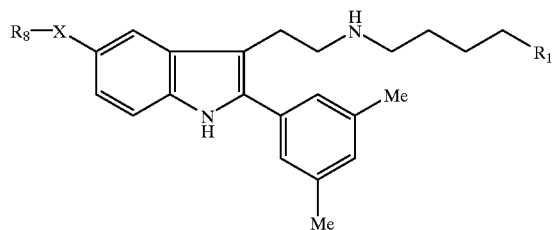

| Example | R₁ | X-R₈ | m/e |
|---|---|---|---|
| 1X | Ph-4-NHEt | O—CO-Piperazine-SO₂—Et | 660 (M + H) |
| 1Y | Ph-4-NH₂ | O—CO-Piperazine-SO₂—Et | 632 (M + H) |
| 1Z | Ph-4-NH—SO₂CH₃ | O—CO-Piperazine-SO₂—Et | 710 (M + H) |
| 1AA | Ph-4-OH | EtO₂S-N(diazepane)-N-C(O)O-Me | 647 (M + H) |
| 1BB | Ph-4-OH | EtOOC-(piperidine)-N-C(O)O-Me | 612 (M + H) |
| 1CC | Ph-4-OH | HOOC-(piperidine)-N-C(O)O-Me | 584 (M+ H) |
| 1DD | Ph-4-OH | O—CO-Piperazine-SO₂—NHMe | 634 (M + H) |
| 1EE | Ph-4-OH | S-(thiomorpholine)-N-C(O)O-Me | 558 (M + H) |
| 1FF | Ph-4-OH | MeO₂S-spiroindoline-piperidine-N-C(O)O-Me | 721 (M + H) |
| 1GG | Ph-4-N(Et)SO₂—NHMe | O—CO-Piperazine-SO₂—Et | — |

EXAMPLE 2.1

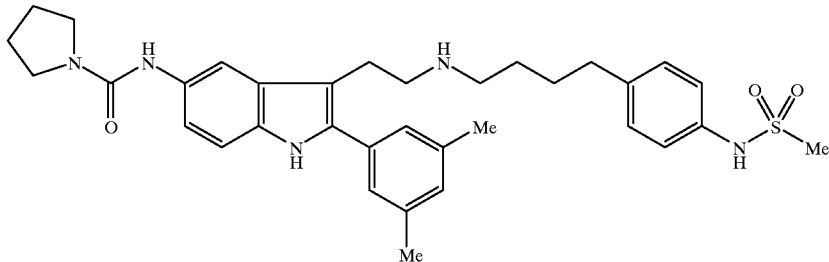

Pyrrolidine-1-carboxylic acid (2-(3,5-dimethylphenyl)-3-{2-[4-(4-methanesulfonylaminophenyl)butylamino]ethyl}-1H-indol-5-yl)amide Step 2.1A N-benzyl-2-[2-(3,5-dimethylphenyl-5-nitro-1H-indol-3-yl]-N-[4-(4-methanesulfonylaminophenyl)butyl]-2-oxo-acetamide To a solution of 2-(3,5-dimethylphenyl)-5-nitro-1H-indole (253 mg in 15 mL dry tetrahydrofuran) was added 0.125 mL oxalyl chloride and the mixture heated to 56° C. on an oil bath. After 14 hours, the mixture was cooled, concentrated in vacuo and the residual oxalyl chloride removed by azeotrope with benzene. The crude material was re-solvated in tetrahydrofuran at 0° C. and treated with a solution of N-[4-(4-benzylaminobutyl)phenyl] methanesulfonamide (347 mg in 5 mL tetrahydrofuran) and 0.22 mL triethylamine then allowed to warm to room temperature. After 1 hour, the mixture was partitioned between ethyl acetate and saturated ammonium chloride and extracted. The organic portion was washed with brine dried over sodium sulfate and the concentrate purified by flash chromatography on silica gel (hexane:ethyl acetate, 4:5; then 2:3) to give the title compound (391 mg).

Step 2.1B N-{4-[4-(benzyl-{2-[2-(3,5-dimethylphenyl)-5-nitro-1H-indol-3-yl]ethyl}amino)butyl]phenyl}methanesulfonamide To a solution of N-benzyl-2-[2-(3,5-dimethylphenyl)-5-nitro-1H-indol-3-yl]-N-[4-(4-methanesulfonylaminophenyl)butyl]-2-oxo-acetamide (391 mg in 20 mL dry tetrahydrofuran) was added 5.5 mL of a 1M solution of borane in tetrahydrofuran and the mixture heated slowly to reflux on an oil bath. After 2 hours the mixture was cooled to room temperature and the excess borane quenched by the careful addition of methanol. The mixture was concentrated to half-volume, treated with N,N-dimethylethanolamine (1.8 mL) and heated to reflux on an oil bath. After 3 hours the mixture was cooled to room temperature and concentrated in vacuo. Purification by flash chromatography on silica gel (hexane:ethyl acetate, 3:2) gave the title compound (317 mg).

Step 2.1C N-{4-[4-({2-[5-amino-2-(3,5-dimethylphenyl)-1H-indol-3-yl]ethyl}benzylamino)butyl]phenyl}methanesulfonamide To a stirred solution of N-{4-[4-(benzyl-{2-[2-(3,5-dimethylphenyl)-5-nitro-1H-indol-3-yl]ethyl}amino)butyl] phenyl} methanesulfonamide (491 mg in 30 mL absolute ethanol) was added ca. 30 mg of Raney® nickel. The reaction flask was fitted with a hydrogen balloon, evacuated and recharged with hydrogen (3 times) and stirred at room temperature. After 2.5 hours the reaction was flushed with nitrogen, filtered over diatomaceous earth and concentrated in vacuo. Purification by flash chromatography on silica gel (hexane:ethyl acetate, 2:3; then 1:3) gave the title compound (344 mg).

Step 2.1D pyrrolidine-1-carboxylic acid [3-(2-{benzyl-[4-(4-methanesulfonylaminophenyl)butyl]amino}ethyl)-2-(3,5-dimethylphenyl)-1H-indol-5-yl]-amide To a stirred solution of N-{4-[4-({2-[5-amino-2-(3,5-dimethylphenyl)-1H-indol-3-yl]ethyl}benzylamino)butyl] phenyl} methanesulfonamide (15 mg in 1.5 mL of dry methylene chloride) was added 0.01 mL pyrrolidinecarbamyl chloride and 0.013 mL diisopropylethylamine and the mixture stirred at room temperature. After 24 hours an additional 0.02 mL of pyrrolidinecarbamyl chloride and 0.26 mL diisopropylethylamine were added. After 6 days (total) the reaction was concentrated in vacuo and purified by flash chromatography on silica gel (methylene chloride:methanol, 95:5) to give the title compound (16 mg).

Step 2.1E pyrrolidine-1-carboxylic acid (2-(3,5-dimethylphenyl)-3-{2-[4-(4-methanesulfonylaminophenyl)butylamino]ethyl}-1H-indol-5-yl)amide To a stirred solution of pyrrolidine-1-carboxylic acid [3-(2-{benzyl-[4-(4-methanesulfonylaminophenyl)butyl] amino}ethyl)-2-(3,5-dimethylphenyl)-1H-indol-5-yl]-amide (16 mg in a mixture of 1 mL tetrahydrofuran and 3 mL methanol) was added 15 mg of 10% palladium hydroxide on carbon catalyst followed by acetic acid (0.015 mL of a 30% solution in water). The reaction flask was fitted with a hydrogen balloon, evacuated and recharged with hydrogen (3 times) and stirred at room temperature. After 25 minutes the reaction was flushed with nitrogen, filtered over diatomaceous earth and concentrated in vacuo. Purification by flash chromatography (methylene chloride:methanol:ammonium hydroxide, 90:8:1) gave the title compound (14 mg). m/e=602 (M+H)

EXAMPLE 2.2

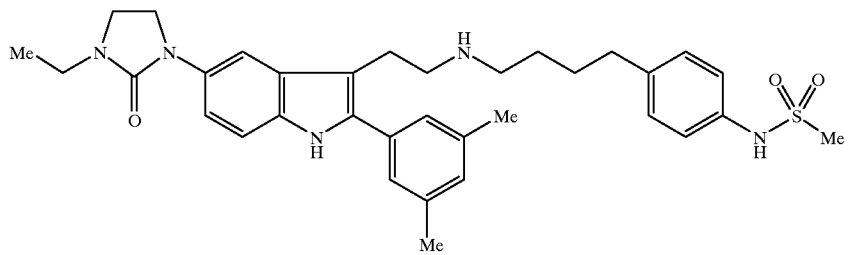

N-[4-(4-{2-[2-(3,5-dimethylphenyl)-5-(3-ethyl-2-oxo-imidazolidin-1-yl)-1H-indol-3-yl]ethylamino}butyl)phenyl]methanesulfonamide Step 2.2A 2-(3,5-dimethylphenyl)-5-amino-1H-indole To a stirred solution of 2-(3,5-dimethylphenyl)-5-nitro-1H-indole (2 g in a mixture of 55 mL tetrahydrofuran and 20 mL methanol) was added 347 mg of 10% palladium hydroxide on carbon catalyst followed by acetic acid (1 mL of a 30% solution in water). The reaction flask was fitted with a hydrogen balloon, evacuated and recharged with hydrogen (3 times) and stirred at room temperature. After 25 hours the flask was charged with an additional 320 mg catalyst and 1 mL of 30% acetic acid and re-subjected to hydrogen. After a total reaction time of 3 days, the mixture was flushed with nitrogen, filtered over diatomaceous earth and concentrated in vacuo. Purification by flash chromatography (hexane:ethyl acetate, 1:1) gave the title compound (1.16 g).

Step 2.2B [2-(3,5-dimethylphenyl)-1H-indol-5-yl]-carbamic acid benzyl ester

To a solution of 2-(3,5-dimethylphenyl)-5-amino-1H-indole (1.16 g in 60 mL dry methylene chloride) at –60 ° C. was added 0.86 mL benzyl chloroformate followed by 1 mL diisopropylethylamine and the mixture warmed slowly to 0° C. After 45 minutes, the reaction was quenched by the addition of saturated aqueous ammonium chloride and the mixture extracted with methylene chloride. The organic portion was washed with brine, dried over sodium sulfate and concentrated in vacuo. Purification by flash chromatography (hexane:methylene chloride:ethyl acetate, 8:8:1; then 7:7:1) gave the title compound (1.68 g).

Step 2.2C [3-benzyl-[4-(4-nitrophenyl)-butyl]aminooxalyl}-2-(3,5-dimethylphenyl)-1H-indol-5-yl]carbamic acid benzyl ester Prepared essentially as described in EXAMPLE 2.1 Step A starting from [2-(3,5-dimethylphenyl)-1H-indol-5-yl]-carbamic acid benzyl ester (1.13 g) and benzyl-[4-(4-nitrophenyl)butyl]amine to give the title compound (1.81 g).

Step 2.2D [3-(2-{benzyl-[4-(4-nitrophenyl)butyl]amino}ethyl)-2-(3,5-dimethylphenyl)-1H-indol-5-yl] carbamic acid benzyl ester Prepared essentially as described in EXAMPLE 2.1 Step B starting from [3-{benzyl-[4-(4-nitrophenyl)-butyl]aminooxalyl}-2-(3,5-dimethylphenyl)- 1H-indol-5-yl] carbamic acid benzyl ester (1.81 g) to give the title compound (1.38 g).

Step 2.2E 3-(2-{benzyl-[4-(4-nitrophenyl)butyl]amino}ethyl)-2-(3,5-dimethylphenyl)-1H-indol-5-ylamine To a solution of [3-(2-{benzyl-[4-(4-nitrophenyl)butyl]amino}ethyl)-2-(3,5-dimethylphenyl)-1H-indol-5-yl] carbamic acid benzyl ester (500 mg in 25 mL dry methylene chloride) was added 0.50 mL anisole followed by 0.035 mL benzyl alcohol and the mixture stirred at room temperature. Then, 2.94 mL of a 1M solution of aluminum chloride in nitrobenzene was added dropwise. After 11.5 hours, the reaction was cooled to 0° C. and quenched by the addition of saturated aqueous sodium bicarbonate and partitioned between ethyl acetate and aqueous sodium potassium tartarate. The organic portion was washed with additional tartarate solution and dried over sodium sulfate. Purification of the concentrate by flash chromatography on silica gel (methylene chloride:methanol, 97:3) gave the title compound (354 mg).

Step 2.2F N-{[3-(2-{benzyl-[4-(4-nitrophenyl)butyl]amino}ethyl)-2-(3,5-dimethylphenyl)-1H-indol-5-ylcarbamoyl]methyl}-acetamide To a solution of acetylaminoacetic acid (32.2 mg in 6 mL dry methylene chloride) was added 48 mg 1-hydroxybenzotriazole followed by 50 mg 1-(3-dimethylaminopropyl)-3-ethylcarbodiimide hydrochloride and the mixture stirred at room temperature. After 50 minutes, a solution of 3-(2-{benzyl-[4-(4-nitrophenyl)butyl]amino}ethyl)-2-(3,5-dimethylphenyl)-1H-indol-5-ylamine (120 mg in 2 mL methylene chloride) was added and stirring continued. After 4 hours (total), the mixture was concentrated in vacuo and purified by flash chromatography on silica gel (methylene chloride:methanol, 95:5) to give the title compound (131 mg).

Step 2.2G N-[3-(2-{benzyl-[4-(4-nitrophenyl)butyl]amino}ethyl)-2-(3,5-dimethylphenyl)-1H-indol-5-yl]-N'-ethyl-ethane-1,2-diamine Prepared essentially as described in EXAMPLE 2.1 Step B starting from N-{[3-(2-{benzyl-[4-(4-nitrophenyl)butyl]amino}ethyl)-2-(3,5-dimethylphenyl)-1H-indol-5-ylcarbamoyl]methyl}acetamide (131 mg) to give the title compound (80 mg).

Step 2.2H 1-[3-(2-{benzyl-[4-(4-nitrophenyl)butyl]amino}ethyl)-2-(3,5-dimethylphenyl)-1H-indol-5-yl]-3-ethylimidazolidin-2-one To a solution of N-[3-(2-{benzyl-[4-(4-nitrophenyl)butyl]amino}ethyl)-2-(3,5-dimethylphenyl)-1H-indol-5-yl]-N'-ethyl-ethane-1,2-diamine (20 mg in 3 mL dry methylene chloride) at 0° C. was added 9.6 mg N,N'-disuccinimidyl carbonate followed by triethylamine (0.110 mL of a 10% solution in methylene chloride) and the mixture stirred at low temperature. After 30 minutes, the reaction was quenched by the addition of saturated aqueous ammonium chloride and extracted with ethyl acetate. The organic portion was washed with saturated sodium bicarbonate, dried over sodium sulfate and concentrated in vacuo to provide the crude title compound (21 mg).

Step 2.2I 1-[3-(2-{[4-(4-aminophenyl)butyl]benzylamino}ethyl)-2-(3,5-dimethylphenyl)-1H-indol-5-yl]-3-ethylimidazolidin-2-one Prepared essentially as described in EXAMPLE 2.1 StepC starting from 1-[3-(2-{benzyl-[4-(4-nitrophenyl)butyl]amino}ethyl)-2-(3,5-dimethylphenyl)-1H-indol-5-yl]-3-ethylimidazolidin-2-one (85 mg) to give the title compound (47.5 mg).

Step 2.2J N-{4-[4-(benzyl-{2-[2-(3,5-dimethylphenyl)-5-(3-ethyl-2-oxo-midazolidin-1-yl)-1H-indol-3-yl]ethyl}amino)butyl]phenyl}-methanesulfonamide To a solution of 1-[3-(2-{[4-(4-aminophenyl)butyl]benzylamino}ethyl)-2-(3,5-dimethylphenyl)-1H-indol-5-yl]-3-ethylimidazolidin-2-one (47.5 mg in 1.5 mL dry methylene chloride) at 0° C. was added methanesulfonyl chloride (0.066 mL of a 10% solution in methylene chloride) followed by triethylamine (0.125 mL of a 10% solution in methylene chloride) and the mixture stirred at low temperature. During the course of 2 hours, additional portions of methanesulfonyl chloride and triethylamine were added, and the reaction quenched after 3 hours by the addition of saturated sodium bicarbonate. The mixture was partitioned between ethyl acetate and water, and the organic portion washed successively with saturated ammonium chloride and saturated sodium bicarbonate, then dried over sodium sulfate. Purification of the concentrate by flash chromatography on silica gel (methylene chloride:methanol: ammonium hydroxide, 95:5:1) gave the title compound (50 mg).

Step 2.2K N-[4-(4-{2-[2-(3,5-dimethylphenyl)-5-(3-ethyl-2-oxo-imidazolidin-1-yl)-1H-indol-3-yl]ethylamino}butyl)phenyl]methanesulfonamide Prepared essentially as described in EXAMPLE 2.1 StepE starting from N-{4-[4-(benzyl-{2-[2-(3,5-dimethylphenyl)-5-(3-ethyl-2-oxo-midazolidin-1-yl)-1H-indol-3-yl]ethyl}amino)butyl]phenyl}-methanesulfonamide (50 mg) to give the title compound (40 mg). m/e=602 (M+H)

Following a procedure similar to that described above, the following compounds are prepared:

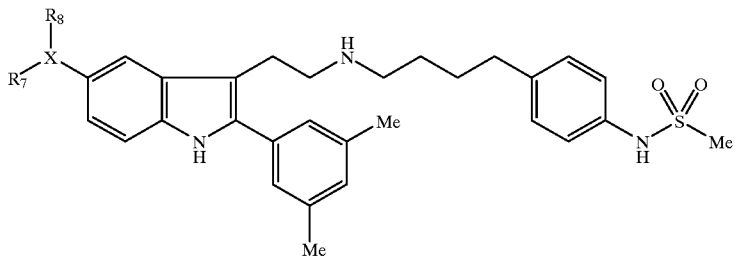

| Ex. | X-R₇, R₈ | m/e |
|---|---|---|
| 2A | EtO₂S-N(piperazine)-C(=O)-NHMe | 709 (M + H) |
| 2B | pyrrolidine-C(=O)-NMe₂ | 616 (M + H) |
| 2C | 3-ethyl-4-methyl-1-methyl-imidazolidin-2-one | 616 (M + H) |
| 2D | 1-phenyl-3-methyl-imidazolidin-2-one | 650 (M + H) |

-continued
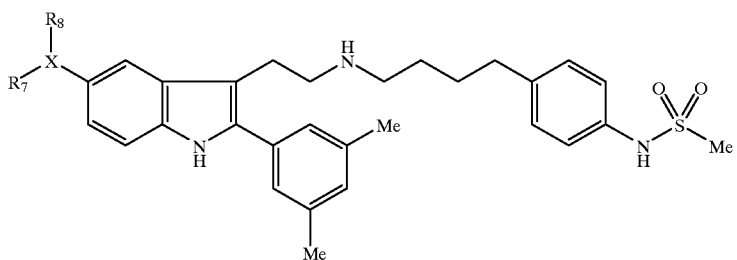
| Ex. | X-R₇, R₈ | m/e |
|---|---|---|
| 2E | (1-cyclopropyl-3-methyl-imidazolidin-2-one) | 614 (M + H) |
| 2F | (1-ethyl-3-methyl-tetrahydropyrimidin-2-one) | 616 (M + H) |
| 2G | (morpholine-4-carboxylic acid dimethylamide) | 632 (M + H) |
| 2H | (morpholine-4-carboxylic acid methylamide) | 618 (M + H) |
| 2I | NH—CO-Piperazine-CONHMe | 674 (M + H) |
| 2J | (pyrimidin-4-yl methylurea) | 626 (M + H) |
| 2K | (thiazol-4-yl methylurea) | 631 (M + H) |

EXAMPLE 3.1

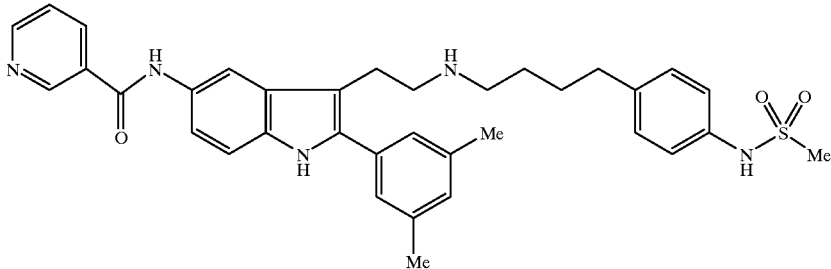

N-(2-(3,5-dimethylphenyl)-3-{2-[4-(4-methanesulfonylaminophenyl)-butylamino]ethyl}-1H-indol-5-yl)nicotinamide Step 3.1A N-[3-(2-{benzyl-[4-(4-methanesulfonylaminophenyl)butyl]-amino}-ethyl)-2-(3,5-dimethylphenyl)-1H-indol-5-yl]-nicotinamide Prepared essentially as described in EXAMPLE 2.2 Step F starting from N-{4-[4-({2-[5-amino-2-(3,5-dimethylphenyl)-1H-indol-3-yl]ethyl}benzylamino)butyl]phenyl}-methanesulfonamide (EXAMPLE 2.1 Step C, 15 mg) to give the title compound (17 mg).

Step 3.1B N-(2-(3,5-dimethylphenyl)-3-{-2-[4-(4-methanesulfonylaminophenyl)-butylamino]ethyl}-1H-indol-5yl)nicotinamide Prepared essentially as described in EXAMPLE 2.1E starting from N-[3-(2-{benzyl-[4-(4-methanesulfonylaminophenyl)butyl]-amino}-ethyl)-2-(3,5-dimethylphenyl)-1H-indol-5-yl]-nicotinamide (17mg) to give the title compound (10 mg). M/E=610 (M+H)

EXAMPLE 3.2

0° C. After 25 minutes, the reaction was quenched by the addition of excess saturated aqueous ammonium chloride and the mixture extracted with ethyl acetate. The organic portion was dried over sodium sulfate and concentrated in vacuo. The residue was purified by flash chromatography on silica gel (hexane:ethyl acetate, 1:1) to give the title compound (990 mg).

Step 3.2B {2-[2-(3,5-dimethylphenyl)-5-nitro-1H-indol-3-yl]-ethyl}-[4-(4-amino(dimethanesulfonyl)phenyl)butyl] carbamic acid tert-butyl ester To a solution of {2-[2-(3,5-dimethylphenyl)-5-nitro-1H-indol-3-yl]ethyl}-[4-(4-methanesulfonylaminophenyl)butyl]carbamic acid tert-butyl ester (300 mg in 7 mL methylene chloride) at 0° C. was added 0.135 mL triethylamine and 0.066 mL methanesulfonyl chloride and the mixture sired at low temperature. After 30 minutes, the reaction was quenched by the addition of saturated aqueous sodium bicarbonate and partitioned between water and ethyl acetate. The organic portion was washed successively with saturated ammonium chloride, saturated sodium bicarbonate and brine, then dried over sodium sulfate and concentrated in vacuo to give the crude title compound (330 mg).

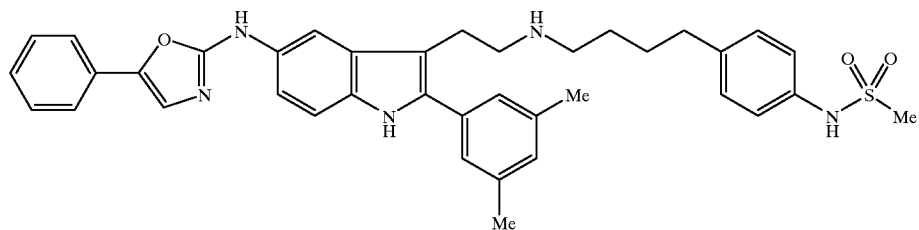

N-[4-(4-{2-[2-(3,5-dimethylphenyl)-5-(5-phenyloxazol-2-ylamino)-1H-indol-3-yl]ethylamino}butyl)phenyl]methanesulfonamide Step 3.2A [2-{2-(3,5-dimethylphenyl)-5-nitro-1H-indol-3-yl]ethyl}-[4-(4-methanesulfonylaminophenyl)butyl] carbamic acid tert-butyl ester To a solution of N-[4-(4-{2-[2-(3,5-dimethylphenyl)-5-nitro-1H-indol-3-yl]ethylamino}butyl)phenyl] methanesulfonamide (prepared essentially as described in EXAMPLE 2.1 StepB, 800 mg in 15 mL tetrahydrofuran and 4 mL water) at 0° C. was added a solution of 580 mg di-tert-butyl dicarbonate followed by 317 mg poatssium carbonate and the resulting suspension stirred vigourously at Step 3.2C {2-[5-amino-2-(3,5-dimethylphenyl)-1H-indol-3-yl]ethyl}-[4-(4-amino(dimethanesulfonyl)phenyl)butyl]carbamic acid tert-butyl ester The title compound was prepared essentially as described in EXAMPLE 2.1 StepE starting from {2-[2-(3,5-dimethylphenyl)-5-nitro-1H-indol-3-yl]-ethyl}-[4-(4-amino(dimethanesulfonyl)phenyl)butyl]-carbamic acid tert-butyl ester (330 mg) and using 10% palladium on carbon as catalyst to give the title compound (286 mg).

Step 3.2D {2-[2-(3,5-dimethylphenyl)-5-isocyanato-1H-indol-3-yl]ethyl}-[4-(4-amino(dimethanesulfonyl)phenyl)butyl]carbamic acid tert-butyl ester To a solution of {2-[5-amino-2-(3,5-dimethylphenyl)-1H-indol-3-yl]ethyl}-[4-(4-amino(dimethanesulfonyl)phenyl)

butyl]carbamic acid tert-butyl ester (120 mg in 8 mL dry methylene chloride) at 0° C. was added 0.040 mL pyridine followed by 18.2 mg triphosgene and the mixture stirred at low temperature. After 20 minutes, 0.025 mL triethylamine was added and after another 10 minutes the mixture was applied to a silica gel column for purification by flash chromatography (hexane:ethyl acetate, 2:3) to give the title compound (106 mg).

Step 3.2E {2-[2-(3,5-dimethylphenyl)-5-(5-phenyloxazol-2-ylamino)-1H-indol-3-yl]-ethyl}-[4-(4-amino(dimethanesulfonyl) phenyl)-butyl]carbamic acid tert-butyl ester To a solution of {2-[2-(3,5-dimethylphenyl)-5-isocyanato-1H-indol-3-yl]ethyl}-[4-(4-amino(dimethanesulfonyl)phenyl)butyl] carbamic acid tert-butyl ester (30 mg in 0.50 mL dry methylene chloride) was added 9 mg of 2-azido-1-phenyl-ethanone followed by 14 mg triphenylphosphine and the mixture stirred at room temperature. After 4 hours, the mixture was applied to a silica gel column for purification by flash chromatography (hexane:ethyl acetate, 3:2; then 1:1; then 2:3; then 1:3) to give the title compound (13 mg).

Step 3.2F {2-[2-(3,5-dimethylphenyl)-5-(5-phenyloxazol-2-ylamino)-1H-indol-3-yl]-ethyl}-[4-(4-methanesulfonylamino phenyl)butyl]-carbamic acid tert-butyl ester To a solution of {2-[2-(3,5-dimethylphenyl)-5-(5-phenyloxazol-2-ylamino)-1H-indol-3-yl]-ethyl}-[4-(4-amino(dimethanesulfonyl)phenyl)-butyl]carbamic acid tert-butyl ester (13 mg in 0.50 mL tetrahydrofuran) was added 0.125 mL of a 1.25N sodium hydroxide solution and the mixture stirred at room temperature. After 30 minutes, the reaction mixture was partitioned between ethyl acetate and water, and the organic portion washed successively with saturated ammonium chloride, saturated sodium bicarbonate and brine. The combined organics were dried over sodium sulfate and concentrated in vacuo and the residue purified by by flash chromatography on silica gel (methylene chloride:methanol, 96:4) to give the title compound (10 mg).

Step 3.2G N-[4-(4-{2-[2-(3,5-dimethylphenyl)-5-(5-phenyloxazol-2-ylamino)-1H-indol-3-yl]ethylamino}butyl) phenyl]-methanesulfonamide To a solution of {2-[2-(3,5-dimethylphenyl)-5-(5-phenyloxazol-2-ylamino)-1H-indol-3-yl]-ethyl}-[4-(4-methanesulfonylaminophenyl)butyl]-carbamic acid tert-butyl ester (10 mg in 0.80 mL methylene chloride) at 0° C. was added 0.050 mL anisole followed by 0.20 mL trifluoroacetic acid and the mixture stirred at 0° C. After 3 hours, the mixture was concentrated in vacuo and the residual acid removed by azeotrope with toluene. Purification of the concentrate by flash chromatography on silica gel (methylene chloride:methanol:ammonium hydroxide, 90:7:1) gave the title compound (8 mg). m/e 648 (M+H)

Following a procedure similar to that described above, the following compounds are prepared:

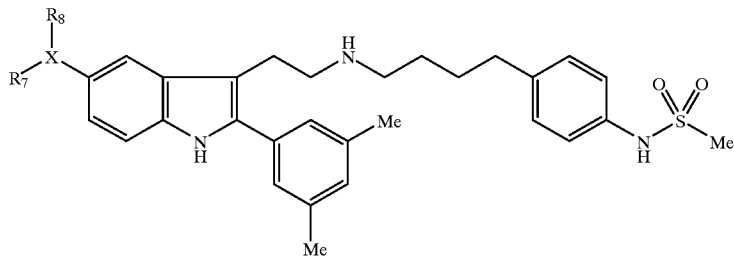

| Example | X-R$_7$R$_8$ | m/e |
|---|---|---|
| 3A | | 649 (M + H) |
| 3B | | 603 (M + H) |
| 3C | | 599 (M + H) |

-continued

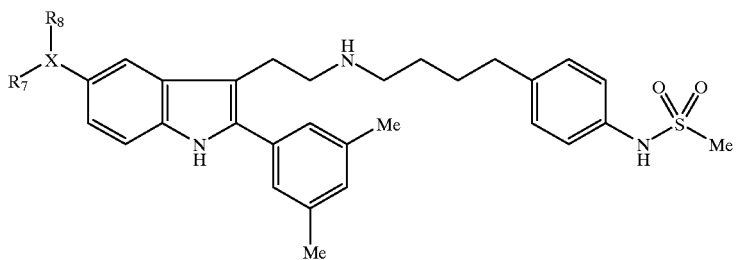

| Example | X-R$_7$R$_8$ | m/e |
|---|---|---|
| 3D | (piperidine-4-carboxylic acid N-methylamide) | 616 (M + H) |
| 3E | (isonicotinic acid N-methylamide) | 610 (M + H) |
| 3F | (picolinic acid N-methylamide) | 610 (M + H) |

EXAMPLE 4

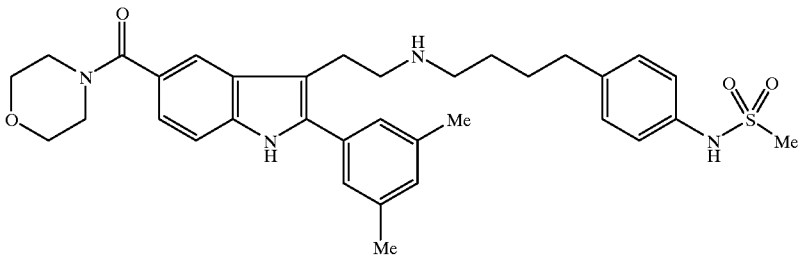

N-[4-[4-[2-[2-(3,5-dimethylphenyl)-5-(morpholine-4-carbonyl)-1H-indol-3-yl]ethylamino]butyl]phenyl]methanesulfonamide Step 4A 3-(2-aminoethyl)-2-(3,5-dimethylphenyl)-1H-indole-5-carboxylic acid ethyl ester A mixture of 7.60 g (50 mmol) of 4-hydrazinobenzoic acid, 10.55 g (50 mmol) of 3-chloropropyl 3,5-dimethylphenyl ketone, and 200 mL of absolute ethanol was stirred under nitrogen and heated to reflux. After 12 hours, the mixture was cooled and filtered. The solid on the filter was washed with additional small volumes of ethanol. The filtrate was treated with 4 mL of concentrated sulfuric acid and stirred at reflux under nitrogen for 4 days. The cooled mixture was stirred in an ice bath as a solution of sodium ethoxide (21 % w/w in ethanol) was added dropwise under nitrogen until the mixture was basic by pH paper. The mixture was filtered and concentrated in vacuo at 30° C. The residue was partitioned between diethyl ether and water, with some saturated aqueous sodium chloride solution added to assist in separation of the layers. The aqueous phase was washed with an additional 100 mL of ether. The combined organic extracts were dried over sodium sulfate, filtered, and concentrated in vacuo. The residual gum was flash chromatographed on silica gel (elution with 97:3:0.3 and then 95:5:0.5 CH$_2$Cl$_2$-MeOH-concentrated NH$_4$OH). Concentration of the product fractions yielded 4.03 g of pure product as a stiff foam (virtually homogeneous by TLC in 95:5:0.5 CH$_2$Cl$_2$-MeOH-concentrated NH$_4$OH). Concentration of mixed fractions yielded an additional 0.93 g, which was rechromatographed to provide an additional 0.77 g of pure material, for a total yield of 4.80 g (29%). 400 MHz $^1$H NMR (CDCl$_3$) was consistent with the assigned structure. Mass spectrum (PB-NH$_3$/CI): m/e=337 (M+H).

Step 4B 2-(3,5-dimethylphenyl)-3-{2-[4-(4-methanesulfonylamino-phenyl)butylamino]ethyl}-1H-indole-5-carboxylic acid ethyl ester To a dry flask were added 672 mg (2.0 mmol) of 3-(2-aminoethyl)-2-(3,5-dimethylphenyl)-1H-indole-5-carboxylic acid ethyl ester, 530 mg (2.2 mmol) of 4-[4-(methanesulfonamido)phenyl]-butyraldehyde, 1.20 g (10 mmol) of magnesium sulfate, and a magnetic stirring bar. The flask was purged with nitrogen, cooled to −10° to −5° C. in an ice-methanol bath, and stirred as 4 mL of dry CDCl$_3$ was introduced gradually by syringe. The mixture was stirred under nitrogen for 15 minutes. Next, the septum was removed, and 100 mg (2.6 mmol) of sodium borohydride was added rapidly. The septum was immediately replaced, and the system was again purged with nitrogen. The mixture was stirred under nitrogen at about −5° C. as 4 mL of dry methanol was added gradually by syringe. After 20 minutes at this temperature, the reaction was quenched by gradual syringe addition of 1 mL of acetone to destroy excess sodium borohydride. After a few more minutes, the mixture was removed from the cooling bath and partitioned between 25 mL of ethyl acetate and 25 mL of water. The organic layer was washed with 10 mL of saturated aqueous sodium chloride solution, then dried over sodium sulfate, filtered, and concentrated in vacuo. The residue was flash chromatographed on silica gel (elution with 97:3 and then 95:5 CH$_2$Cl$_2$-MeOH). Concentration of the pooled product fractions in vacuo yielded 663 mg (59%) of a foam; virtually homogeneous by TLC (92.5:7.5 CH$_2$Cl$_2$-MeOH). 400 MHz $^1$H NMR (CDCl$_3$+ small amount of DMSO-d$_6$) was consistent with the assigned structure. Mass spectrum (ESI): m/e=562 (M+H).

Step 4C 3-(2-{benzyloxycarbonyl-[4-(4-methanesulfonylamino-phenyl)butyl]amino}ethyl)-2-(3,5-dimethylphenyl)-1H-indole-5-carboxylic acid ethyl ester A solution of 646 mg (1.15 mmol) of 2-(3,5-dimethylphenyl)-3-{2-[4-(4-methanesulfonylamino-phenyl)butylamino]ethyl}-1H-indole-5-carboxylic acid ethyl ester in 5 mL of dry methylene chloride and 5 mL of anhydrous tetrahydrofuran was stirred under nitrogen and cooled to −78° C. in a dry ice-acetone bath as 200 mL of N,N-diisopropylethylamine was added, followed by gradual addition of 173 mL (207 mg; 1.15 mmol, based on 95% purity) of benzyl chloroformate was added gradually by syringe. After 30 minutes, the solution was removed from the cooling bath and allowed to warm to room temperature. It was then partitioned between 25 mL of ethyl acetate and 25 mL of 5% potassium bisulfate aqueous solution. The organic layer was washed with an additional 25 mL of 5% potassium bisulfate and then with 10 mL of saturated aqueous sodium chloride solution. The organic phase was dried (magnesium sulfate), filtered, and concentrated in vacuo. Flash chromatography of the residue on silica gel (elution with 98:2 CH$_2$Cl$_2$-MeOH) afforded 611 mg (76%) of a foam; homogeneous by TLC in 95:5 CH$_2$Cl$_2$-MeOH. 500 MHz $^1$H NMR was complex, owing to the existence of rotamers, but was consistent with the assigned structure. Mass spectrum (ESI): m/e=696 (M+H).

Step 4D 3-(2-{benzyloxycarbonyl-[4-(4-methanesulfonylamino-phenyl)butyl]amino}ethyl)-2-(3,5-dimethylphenyl)-1Hindole-5-carboxylic acid A solution of 600 mg (0.862 mmol) of 3-(2-{benzyloxycarbonyl-[4-(4-methanesulfonylamino-phenyl)butyl]amino}ethyl)-2-(3,5-dimethylphenyl)-1H-indole-5-carboxylic acid ethyl ester in 18 mL (9 mmol) of 0.50N potassium hydroxide in methanol was stirred at about 60° C. as 2.0 mL of water was added gradually. Stirring was continued at 60°–65° C. under nitrogen for 10 hours. The cooled mixture, which contained a white precipitate, was concentrated to small volume in vacuo. The residual suspension was partitioned between 25 mL of ethyl acetate and 25 mL of 0.5N hydrochloric acid. After the aqueous layer was separated, precipitation began in the ethyl acetate phase. Dilution with 25 mL of tetrahydrofuran redissolved the precipitate. The aqueous phase was back-extracted with 10 mL of ethyl acetate+10 mL of tetrahydrofuran. The combined organic phases were dried over magnesium sulfate, filtered, and concentrated in vacuo. The residual solid was triturated with diethyl ether, collected on a filter, and washed with some additional ether to give (after drying) 573 mg (100%) of a powder, mp 211.5°–213° C.; virtually homogeneous by TLC(92.5:7.5 CH$_2$Cl$_2$-MeOH). 500 MHz $^1$H NMR (DMSO-d$_6$) was consistent with the assigned structure. Mass spectrum (ESI): m/e=668 (M+H).

Step 4E [2-[2-(3,5-dimethylphenyl)-5-(morpholine-4-carbonyl)-1H-indol-3-yl]ethyl]-[4-[4-(methanesulfonylamino)phenyl]-butyl]carbamic acid benzyl ester A mixture of 33.4 mg (0.050 mmol) of [3-[2-[benzyloxycarbonyl-[4-[4-(methanesulfonylamino)phenyl]butyl]amino]-ethyl]-2-(3,5-dimethylphenyl)-1H-indole-5-carboxylic acid, 26.0 mg (0.050 mmol) of PyBOP reagent, 0.010 mL (7.3 mg, 0.072 mmol) of triethylamine, 0.0065 mL (6.5 mg, 0.075 mmol) of morpholine, and 0.0400 mL of dry methylene chloride was stirred under nitrogen at room temperature in a stoppered flask. After 5.5 hours, the solution was partitioned between ethyl acetate and saturated aqueous sodium bicarbonate solution. The organic phase was dried over sodium sulfate, filtered, and concentrated in vacuo. Purification of the crude product by preparative tlc on 2 1000-micron silica gel GF plates (developed in 93:7 CH$_2$Cl$_2$) afforded a quantitative yield amorphous, white solid; homogeneous by TLC in 95:5 CH$_2$Cl$_2$-MeOH. 500 MHz $^1$H NMR (CDCl$_3$) was complex, owing to rotamers, but was consistent with the assigned structure. Mass spectrum (ESI): m/e=737.2 (M+H).

Step 4F N-[4-[4-[2-[2-(3,5-dimethylphenyl)-5-(morpholine-4-carbonyl)-1H-indol-3yl]ethylamino]butyl]phenyl]-methanesulfonamide A mixture of 38 mg (0.05 mmol) of [2-[2-(3,5-dimethylphenyl)-5-(morpholine-4-carbonyl)-1H-indol-3-yl]ethyl]-[4-[4-(methanesulfonylamino)phenyl]butyl]carbamic acid benzyl ester, 10 mg of 20% palladium hydroxide on carbon, and 10 mL of 2-methoxyethanol was shaken with hydrogen (approx. 45 psig) in a pressure vessel for several hours. The catalyst was removed by filtration through Celite, and the filtrate was concentrated in vacuo. The residue was purified by preparative TLC on 2 1000-micron silica gel GF plates (developed in 93:7 CH$_2$Cl$_2$) yielded 17 mg (56%) solid, mp>138° C. dec. (preliminary softening); homogeneous by TLC in 90:10 CH$_2$Cl$_2$-MeOH. 500 MHz $^1$H NMR (CDCl$_3$) was consistent with the assigned structure. Mass spectrum (ESI): m/e=603.3 (M+H).

PREPARATION OF SYNTHETIC INTERMEDIATES

Step A 4-chloro-N-methoxy-N-methylbutyramide

To a solution of 4-chlorobutyryl chloride (10.0 g in 200 mL of dry methylene chloride) was added 10.4 g of N,O-dimethylhydroxylamine hydrochloride. The mixture was stirred under nitrogen and maintained below 25° C. by cooling in an ice bath as necessary while triethylamine (29.1 mL) was added dropwise over about 20 minutes, resulting in precipitation. After 1.5 hours at room temperature, the mixture was concentrated in vacuo. The residue was partitioned between 100 mL of diethyl ether and 100 mL of saturated aqueous sodium bicarbonate solution. The organic layer was washed with an additional 100 mL of saturated sodium bicarbonate, and the aqueous fractions were back-extracted with ether. The combined organic phases were dried over sodium sulfate, filtered, and concentrated in vacuo to give 10.5 g (90%) of an oil, which had satisfactory purity by $^1$H NMR (CDCl$_3$). Mass spectrum (PB-NH$_3$/CI): m/e=166 (M+H).

Step B 3-chloropropyl 3,5-dimethylphenyl ketone

A solution of 10.2 mL (13.9 g; 72 mmol) 5-bromo-m-xylene in 200 mL of anhydrous tetrahydrofuran was stirred under nitrogen at −78° C. as 35.8 mL (84 mmol) of 2.5 M n-butyllithium in tetrahydrofuran was added dropwise. After 15 minutes at −78° C. a solution of 10.0 g (60 mmol) of 4-chloro-N-methoxy-N-methylbutyramide in 30 mL of anhydrous tetrahydrofuran was added dropwise over 25–30 minutes. The resulting solution was maintained at −78° C. for 45 minutes and then warmed briefly to room temperature. The reaction was quenched by addition of 40 mL of 2N hydrochloric acid and then partitioned between ethyl acetate and water. The organic phase was washed with saturated aqueous sodium bicarbonate solution and then saturated aqueous sodium chloride solution. The organic solution was dried over sodium sulfate, filtered, and concentrated in vacuo. Flash chromatography of the residue afforded 8.91 g (70%) of an oil, which had satisfactory purity by $^1$H NMR (CDCl$_3$).

Step AA 4-(4-nitrophenyl)butyric acid, N-methoxy-N-methylamide

A stirred solution of 6.29 g (30 mmol) of 4-(4-nitrophenyl)butyric acid in 90 mL of dry methylene chloride (maintained under nitrogen and cooled in a water bath) was treated with 4.17 mL (3.03 g; 30 mmol) of triethylamine, followed by 13.26 g (30 mmol) of BOP reagent. After a few minutes, 3.22 g (33 mmol) of N,O-dimethylhydroxylamine hydrocholoride was added, followed by an additional 4.59 mL (3.33 g, 33 mmol) of triethylamine. After 2.25 hours, the solution was diluted with 200 mL of diethyl ether and washed successively with 3×100 mL of 2N hydrochloric acid, 1×100 mL and 2×50 mL of saturated aqueous sodium bicarbonate solution, and 1×50 mL of saturated aqueous sodium chloride solution. The organic phase was dried over magnesium sulfate, filtered, and concentrated in vacuo. Flash chromatography of the residue on silica gel (elution with 2:1 and then 3:2 hexane-EtOAc) afforded 6.27 g (83%) of crystals, mp 39.5°–41.5° C.; homogeneous by TLC in 1:1 hexane-EtOAc. 500 MHz $^1$H NMR (CDCl$_3$) was consistent with the assigned structure. Mass spectrum (PB-NH$_3$/CI): m/e=253 (M+H).

Step BB 4-(4-aminophenyl)butyric acid, N-methoxy-N-methylamide

A mixture of 6.05 g (24 mmol) of 4-(4-nitrophenyl) butyric acid, N-methoxy-N-methylamide, 50 mg of 10% palladium on carbon, and 200 mL of ethanol was shaken with hydrogen (initial hydrogen pressure 53 psig) for 1.5 hours, by which time hydrogen uptake had ceased and TLC indicated complete reaction. The mixture was filtered through Celite under nitrogen, and the filtrate was concentrated in vacuo to yield 5.29 g of an oil; homogeneous by TLC in 95:5 CH$_2$Cl$_2$-MeOH. 400 MHz $^1$H NMR (CDCl$_3$) was consistent with the assigned structure. Mass spectrum (PB-NH$_3$/CI): m/e=223 (M+H).

Step CC 4-[4-(methanesulfonamido)phenyl]butyric acid. N-methoxy-N-methylamide

A solution of 5.33 g (24 mmol) of 4-(4-aminophenyl) butyric acid, N-methoxy-N-methylamide in 48 mL of dry pyridine was stirred under nitrogen with cooling in an ice bath as 1.86 mL (2.75 g; 24 mmol) of methanesulfonyl chloride was added dropwise over about 15 minutes. After completion of the addition, the solution was allowed to warm to room temperature. After 1.5 hours, the solution was concentrated in vacuo at room temperature. The residue was diluted with 10 mL of methylene chloride and partitioned between a mixture of 100 mL of ethyl acetate+100 mL of tetrahydrofuran and 100 mL of 2N hydrochloric acid. The organic layer was washed with an additional 4×100 mL of 2N hydrochloric acid, then with 50 mL of saturated aqueous sodium bicarbonate solution, and finally with 20 mL of saturated aqueous sodium chloride solution. The organic phase was diluted with some tetrahydrofuran, dried over magnesium sulfate, and treated with charcoal. The mixture was filtered through Celite, and the filter cake was washed with additional THF. Concentration of the filtrate in vacuo gave 4.39 g (61%) of crystals, mp 115°–117° C.; homogeneous by TLC in 95:5 CH$_2$Cl$_2$-MeOH. 400 MHz $^1$H NMR (DMSO-d$_6$) was consistent with the assigned structure. Mass spectrum (PB-NH$_3$/CI): m/e=301 (M+H).

Step DD 4-[4-(methanesulfonamido)phenyl] butyraldehyde

A mixture of 4.20 g (14 mmol) of 4-[4-(methanesulfonamido)phenyl]butyric acid, N-methoxy-N-methylamide and 100 mL of anhydrous tetrahydrofuran was stirred under nitrogen with cooling in an ice bath as 17.5 mL (17.5 mmol) of 1M lithium aluminum hydride in tetrahydrofuran was added gradually by syringe. After 0.75 hours, 70 mL of 5% potassium hydrogen sulfate solution (aqueous) was added cautiously by syringe. The mixture was then removed from the ice bath, diluted with 150 mL of water, and shaken with 150 mL of ethyl acetate. The milky aqueous phase was extracted with an additional 50 mL of ethyl acetate. The combined organic fractions were washed successively with 2×100 mL of 1N hydrochloric acid, then 50 mL of saturated aqueous sodium bicarbonate solution, and finally 50 mL of saturated aqueous sodium chloride solution. The organic phase was dried over magnesium sulfate, filtered, and concentrated in vacuo. Flash chromatography of the residue on silica gel (elution with 3:2 hexane-EtOAc) yielded 2.47 g (73%) of an oil; homogeneous by TLC in 1:1 hexane-EtOAc. Upon storage in the freezer, solidification occurred (mp 41°–44° C.). 400 MHz $^1$H NMR (CDCl$_3$) was consistent with the assigned structure. Mass spectrum (PB-NH$_3$/CI): m/e=259 (M+NH$_4$).

Following a procedure similar to that described above, the following compounds were prepared:

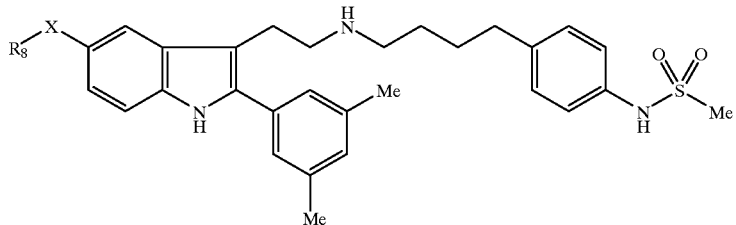
| Example | X-R$_8$ | m/e |
|---|---|---|
| 4A | 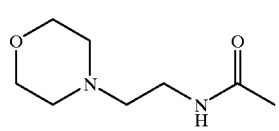 | 646 (M + H) |
| 4B | 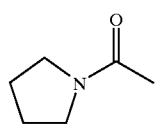 | 587 (M + H) |
| 4C | 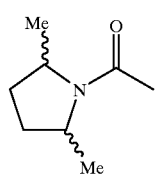 | 615 (M + H) |
| 4D | 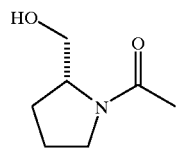 | 617 (M + H) |
| 4E | 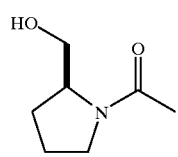 | 617 (M + H) |

-continued
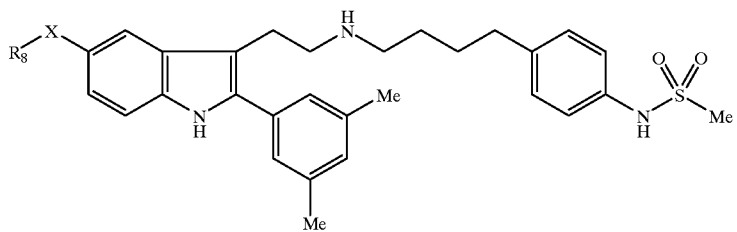
| Example | X-R$_8$ | m/e |
|---|---|---|
| 4F | 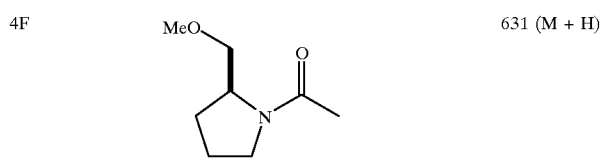 | 631 (M + H) |
| 4G | 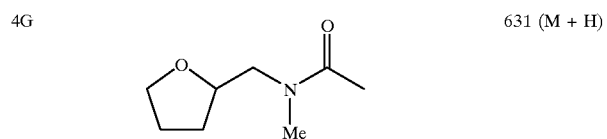 | 631 (M + H) |
| 4H | 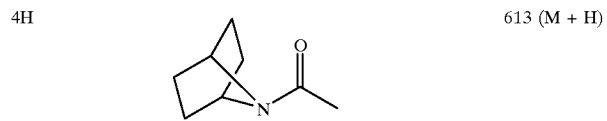 | 613 (M + H) |
| 4I | 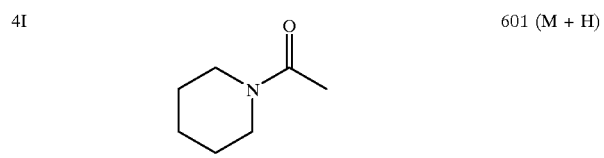 | 601 (M + H) |
| 4J | 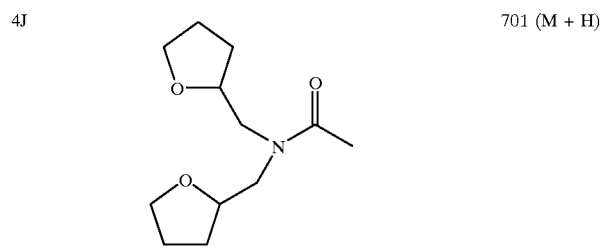 | 701 (M + H) |

EXAMPLE 5

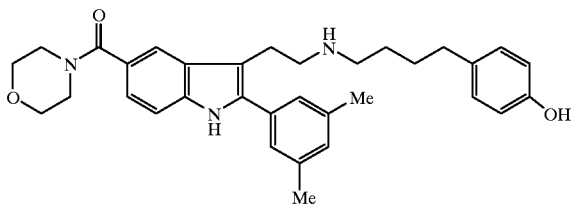

(2-(3,5-dimethylphenyl)-3-{2-[4-(4-hydroxyphenyl)butylamino]ethyl}-1H-indol-5-yl)-morpholin-4-yl-methanone Prepared essentially as described in EXAMPLE 4 m/e=526 (M+H)

EXAMPLE 6.1

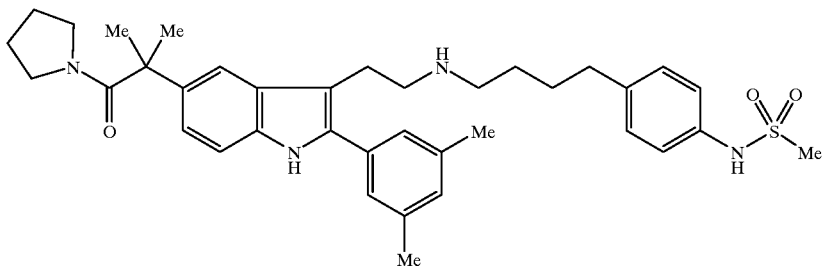

N-[4-[4-[2-[5-(1,1-dimethyl-2-oxo-2-pyrrolidin-1-ylethyl)-2-(3,5-dimethylphenyl)-1H-indol-3-yl]ethylamino]butyl]phenyl]methanesulfonamide Step 6.1A 2-[3-(2-aminoethyl)-2-(3,5-dimethylphenyl)-1H-indol-5-yl]-2-methylpropionic acid ethyl ester By the procedure of Example 4 Step A, ethyl 2-(4-hydrazinophenyl)-2-methylpropionate was reacted with 3-chloropropyl 3,5-dimethylphenyl ketone to afford the titled compound in 16% yield as a stiff foam; virtually homogeneous by TLC in 95:5:0.5 $CH_2Cl_2$-MeOH-concentrated $NH_4OH$. 500 MHz $^1H$ NMR ($CDCl_3$) was consistent with the assigned structure. Mass spectrum (PB-$NH_3$/CI): m/e=379 (M+H)$^+$.

Step 6.1B 2-(2-(3,5-dimethylphenyl)-3-{2-[4-(4-methanesulfonylamino-phenyl)butylamino]ethyl}-1H-indol-5yl)-2-methylpropionic acid ethyl ester The reductive amination reaction of 2-[3-(2-aminoethyl)-2-(3,5-dimethylphenyl)-1H-indol-5-yl]-2-methylpropionic acid ethyl ester and 4-[4-(methanesulfonamido)phenyl]butyraldehyde was carried out according to the procedure of Example 4 Step B to give the titled compound in 43% yield as a stiff foam; virtually homogenous by TLC in 92.5:7.5 $CH_2Cl_2$-MeOH. 500 MHz $^1H$ NMR ($CDCl_3$) was consistent with the assigned structure. Mass spectrum (PB-$NH_3$/CI): m/e=604 (M+H).

Step 6.1C 2-[3-(2-{benzyloxycarbonyl-[4-(4-methanesulfonylamino-phenyl)butyl]amino}ethyl)-2-(3,5-dimethyl-phenyl)-1H-indol-5-yl]-2-methylpropionic acid ethyl ester The reaction of 2-(2-(3,5-dimethylphenyl)-3-{2-[4-(4-methanesulfonylaminophenyl)butylamino]ethyl}-1H-indol-5-yl)-2-methylpropionic acid ethyl ester with benzyl chloroformate was carried out according to the procedure of Example 4, Step C, to give the titled compound in 72% yield as a stiff foam; homogeneous by TLC in 95:5 $CH_2Cl_2$-MeOH. 500 MHz $^1H$ NMR was complex, owing to the existence of rotamers, but was consistent with the assigned structure. Mass spectrum (ESI): m/e=738 (M+H).

Step 6.1D 2-[3-(2-{benzyloxycarbonyl-[4-(4-methanesulfonylamino-phenyl)butyl]amino}ethyl)-2-(3,5-dimethylphenyl)-1H-indol-5yl]-2-methylpropionic acid The saponification of 2-[3-(2-{benzyloxycarbonyl-[4-(4-methanesulfonylamino-phenyl)butyl]amino}ethyl)-2-(3,5-dimethyl-phenyl)-1H-indol-5-yl]-2-methylpropionic acid ethyl ester was achieved according to the procedure of Example 4, Step D, except that the reaction time was increased to 30 hours, providing a quantitative yield of the titled compound as a powder, mp>102° C. (gradual; partial decomposition); homogeneous by TLC in 92.5:7.5 $CH_2Cl_2$-MeOH. 500 MHz $^1H$ NMR (DMSO-$d_6$) was complex, owing to rotamers, but was consistent with the assigned structure. Mass spectrum (ESI): m/e=710 (M+H).

Step 6.1E [2-[5-(1,1-dimethyl-2-oxo-2-pyrrolidin-1-ylethyl)-2-(3,5-dimethylphenyl)-1H-indol-3-yl]ethyl]-[4-(4-methane-sulfonylaminophenyl)butyl]carbamic Acid Benzyl Ester A mixture of 60.4 mg (0.085 mmol) of [3-[2-[benzyloxycarbonyl-[4-[4-(methanesulfonylamino)phenyl]butyl]amino]ethyl]-2-(3,5-dimethylphenyl)-1H-indole-5-yl]-2-methylpropionic acid 46.8 mg (0.09 mmol) of PyBOP reagent, 0.042 mL (36.3 mg, 0.51 mmol) of pyrrolidine, and 0.400 mL of dry methylene chloride was stirred under nitrogen at room temperature in a stoppered flask. After 21 hours, the solution was partitioned between ethyl acetate and 0.5N hydrochloric acid. The organic layer was washed with saturated aqueous sodium bicarbonate solution, then dried over sodium sulfate, filtered, and concentrated in vacuo. Purification of the crude product by preparative TLC on 4 1000-micron silica gel GF plates (developed in 92.5:7.5 $CH_2Cl_2$-MeOH; product band extracted with the same solvent) afforded 55.0 mg (85%) of a nearly colorless stiff foam or glass; satisfactory purity by TLC in 95:5 $CH_2Cl_2$-MeOH. 500 MHz $^1H$ NMR ($CDCl_3$) was complex, owing to rotamers, but was consistent with the assigned structure. Mass spectrum (ESI): m/e=763.7 (M+H)$^+$.

Step 6.1F N-[4-[4-[2-[5-(1,1-dimethyl-2-oxo-2-pyrrolidin-1-ylethyl)-2-(3,5-dimethylphenyl)-1H-indol-3-yl]ethylamino]butyl]-phenyl]methane-sulfonamide A mixture of 52.6 mg (0.069 mmol) of [2-[5-(1,1-dimethyl-2-oxo-2-pyrrolidin-1-ylethyl)-2-(3,5-dimethylphenyl)-1H-indol-3-yl]ethyl]-[4-(4-methanesulfonylaminophenyl)butyl]carbamic acid benzyl ester (from Step 1), 25 mg of 20% palladium hydroxide on carbon, 2.5 mL of ethanol, 2.5 mL of ethyl acetate, and 0.010 mL of glacial acetic acid was shaken with hydrogen (approx.

45 psig) in a pressure vessel for 1.8 hours. The catalyst was removed by filtration through Celite, and the filtrate was concentrated in vacuo. The residue was purified by preparative TLC on 4 Analtech tapered silica gel GF plates (developed in 92.5:7.5:0.75 $CH_2Cl_2$-MeOH-concd. $NH_4OH$; product band extracted with the same solvent) yielded 38.4 mg (88%) of cream-colored, stiff foam; homogeneous by TLC in in 92.5:7.5:0.75 $CH_2Cl_2$-MeOH-concd. $NH_4OH$. 500 MHz $^1H$ NMR ($CDCl_3$) was consistent with the assigned structure. Mass spectrum (ESI): m/e 629.6 $(M+H)^+$.

PREPARATION OF SYNTHETIC INTERMEDIATES

Step A ethyl 2-(4-hydrazinophenyl)acetate hydrochloride and 2-(4-hydrazinophenyl)acetic acid hydrochloride This compound (a mixture of the ethyl ester and the carboxylic acid) was prepared from 13.4 g (75 mmol) of ethyl 2-(4-aminophenyl)acetate, by diazotization and stannous chloride reduction of the diazonium salt, according to the method of L. J. Street, et al., *J. Med. Chem.*, 36, 1529 (1993). The material was obtained in two crops. The first crop consisted of 6.40 g of powder, mp>200° C. By 400 MHz $^1H$ NMR (DMSO-$d_6$), this material consisted of a mixture of carboxylic acid and ethyl ester in approximately a 4:3 molar ratio. Mass spectrum (PB-$NH_3$/CI): 195 (arylhydrazonium cation for the ethyl ester). The second crop consisted of 4.60 g of powder, mp>180° C. By 400 MHz $^1H$ NMR (DMSO-$d_6$), this material consisted of a mixture of carboxylic acid and ethyl ester in approximately a 7:1 molar ratio. After adjustment for the mixture composition of the two crops, the estimated total yield was 69%. Because esterification of any carboxylic acid occurs in the next step, both the ester and the acid react to give the same product.

Step AA Ethyl (±)-2-(4-nitrophenyl)propionate

To a solution of 9.76 g (50 mmol) of (±)-2-(4-nitrophenyl) propionic acid in 150 mL of absolute ethanol was added 3.0 mL of concentrated sulfuric acid. The resulting solution was stirred at reflux under nitrogen. After 6 hours, the solution was cooled and stirred vigorously as 250 mL of saturated aqueous sodium bicarbonate solution was added gradually (Caution: foaming). The mixture was then partitioned between 750 mL of ethyl acetate and 500 mL of water. The organic layer was washed with 100 mL of saturated aqueous sodium bicarbonate solution and then with 100 mL of saturated aqueous sodium chloride solution. The organic phase was dried over magnesium sulfate, filtered, and concentrated in vacuo to give 10.86 g (97%) of an oil; homogeneous by TLC in 9:1 hexane-ethyl acetate. 400 MHz $^1H$ NMR ($CDCl_3$) was consistent with the assigned structure.

Step BB Ethyl 2-methyl-2-(4-nitrophenylpropionate

A suspension of 924 (23 mmol) of sodium hydride (60% in oil) in 21 mL of dry N,N-dimethylformamide was stirred under nitrogen in an ice bath as a solution of 4.68 g (21 mmol) of ethyl (±)-2-(4-nitrophenyl)propionate in 20.5 mL of dry N,N-dimethylformamide was added gradually over about 10 minutes. An intense violet color developed during the addition. The mixture was then allowed to warm to room temperature. After about 1 hour, the mixture was again cooled in an ice bath as a solution of 1.44 mL (3.28 g; 23 mmol) of iodomethane in 5 mL of dry N,N-dimethylformamide was added dropwise by syringe over about 10 minutes, while maintaining the internal temperature at 10°–15° C. The mixture was allowed to warm to room temperature, and the color changed to brown. After 1 hour, an additional 187 mL (426 mg, 3 mmol) of iodomethane was added. By the next day, the mixture consisted of a suspension of some grayish solid in a golden liquid. It was stirred vigorously and quenched by gradual addition of 10 mL of 5% aqueous potassium bisulfate solution. The mixture was partitioned between 400 mL of diethyl ether and 400 mL of water. The organic layer was washed with an additional 3×400 mL of water and then with 50 mL of saturated aqueous sodium chloride solution. The organic phase was then dried over magnesium sulfate, filtered, and concentrated in vacuo. Flash chromatography of the residue on silica gel (elution with 19:1 hexane-ethyl acetete) yielded 4.31 g (87%) of an oil; homogeneous by TLC in 9:1 hexane-ethyl acetete. 400 MHz $^1H$ NMR ($CDCl_3$) was consistent with the assigned structure.

Step CC Ethyl 2-(4-aminophenyl-2-methylpropionate

A mixture of 4.27 g (18 mmol) of ethyl 2-methyl-2-(4-nitrophenyl)propionate, 200 mg of 10% palladium on carbon, and 120 mL of absolute ethanol was shaken with hydrogen (initial hydrogen pressure 47 psig) in a pressure vessel for 2 hours. The catalyst was removed by filtration through Celite under nitrogen, and the filter cake was washed with additional ethanol. Concentration of the filtrate in vacuo at up to 50° C. gave 3.74 g (100%) of an oil; homogeneous by TLC in 4:1 hexane-EtOAc. 400 MHz $^1H$ NMR ($CDCl_3$) was consistent with the assigned structure. Mass spectrum (ESI): m/e=208 (M+H).

Step DD Ethyl 2-(4-hydrazinophenyl)-2-methylpropionate

A solution of 3.725 g (18 mmol) of ethyl 2-(4-aminophenyl)-2-methylpropionate in 18 mL of concentrated hydrochloric acid was stirred at −10° to −5° C. in an ice-acetone bath as a solution of 1.29 g (18.7 mmol) of sodium nitrite in 7.5 mL of water was added dropwise over about 15 minutes. Stirring was continued at this temperature for an additional 30 minutes. Next, a small amount of insoluble solid was removed by filtration into a cold receiving flask. The filtrate was then added dropwise over 10–15 minutes to a solution of 20.3 g (90 mmol) of stannous chloride dihydrate in 14.5 mL of concentrated hydrochloric acid stirred under nitrogen in an ice-acetone bath. The addition was carried out at such a rate that the internal temperature remained at about −5° C. A gummy material separated during the addition. After completion of the addition, stirring was continued at −10° to −5° C. for 1 hour. The aqueous phase was decanted, and the residual gum was dissolved in 250 mL of ethyl acetate. The ethyl acetate solution was treated cautiously with 250 mL of saturated aqueous sodium bicarbonate solution and shaken in a separatory funnel. The ethyl acetate layer was washed with 50 mL of saturated aqueous sodium chloride solution. The entire mixture was filtered before separation of the phases. The ethyl acetate phase was dried over magnesium sulfate, filtered, and concentrated in vacuo at room temperature to yield 2.59 g (65%) of an oil. 500 MHz $^1H$ NMR ($CDCl_3$) was consistent with the assigned structure and indicated that only minor impurities were present.

EXAMPLE 6.2

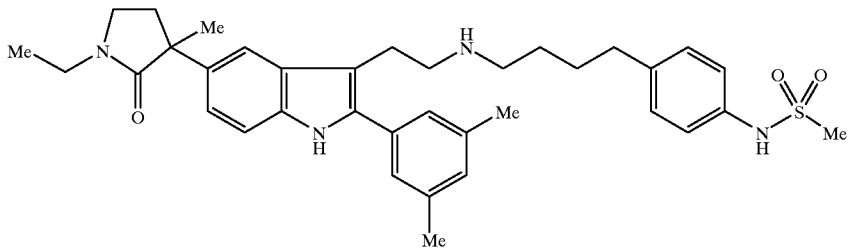

N-[4-[4-[2-[2-(3,5-dimethylphenyl)-5-(1-ethyl-3-methyl-2-oxopyrrolidin-3-yl)-1H-indol-3-yl]ethylamino]butyl]phenyl]-methanesulfonamide Step 6.2A (±)-N-ethyl-N-(2-hydroxyethyl)-2-(4-nitrophenyl)propionamide A solution of 1.95 g. (10 mmol) of (±)-2-(4-nitrophenyl)propionic acid and 5.46 g (10.5 mmol) of PyBOP reagent in 40 mL of dry methylene chloride was stirred under nitrogen with cooling in an ice water bath. To this was added 4.87 mL (4.46 g, 50 mmol) of 2-(ethylamino)ethanol. After 10 minutes, the cooling bath was removed, and the solution was allowed to warm to room temperature. After 4 days, the solution was partitioned between diethyl ether and 0.5N hydrochloric acid. The organic layer was washed with saturated aqueous sodium bicarbonate solution and then with saturated aqueous sodium chloride solution. The organic phase was dried over magnesium sulfate and concentrated in vacuo. The residue was flash chromatographed on silica gel (elution with 99:1 and then 98:2 $CH_2C_2$-MeOH) to yield 1.87 g (70%) of pale yellow, viscous oil; satisfactory purity by TLC in 95:5:0.5 $CH_2Cl_2$-MeOH-AcOH. 500 MHz $^1$H NMR ($CDCl_3$) was complex, owing to rotamers, but consistent with the assigned structure. Mass spectrum ($PB-NH_3/CI$): m/e=267.2 (M+H).

Step 6.2B (±)-1-ethyl-3-methyl-3-(4-nitrophenyl)pyrrolidin-2-one

A solution of 1.73 g (6.5 mmol) of (±)-N-ethyl-N-(2-hydroxyethyl)-2-(4-nitrophenyl)propionamide in 17 mL of anhydrous tetrahydrofuran was stirred under nitrogen and cooled in an ice bath as 1.36 mL (985 mg, 9.75 mmol) of triethylamine was added, followed by dropwise addition of 0.554 mL (819 mg, 7.15 mmol) of methanesulfonylchloride. After completion of the addition, the mixture was removed from the cooling bath and allowed to stir at room temperature in a stoppered flask. After 44 hours, the mixture was diluted with 125 mL of diethyl ether and shaken for a few minutes. The mixture was filtered under nitrogen and washed with some additional diethyl ether. The filtrate was concentrated in vacuo to give 1.85 g of the crude methanesulfonate as a reddish oil. In a dried flask, 312 mg (7.8 mmol) of sodium hydride (60% in oil) was stirred under nitrogen as 10 mL of anhydrous tetrahydrofuran was added by syringe. The resulting suspension was stirred in an ice bath under nitrogen as a solution of the crude methanesulfonate in 10 mL of anhydrous tetrahydrofuran was added dropwise over about 45 minutes. After 20 hours, the dark brown mixture was quenched by dropwise addition of a small amount of glacial acetic acid, until the color changed to a lighter orange. After a few minutes, the mixture was diluted with about 50 mL of ether and stirred some more. The insoluble salts were removed by filtration (filter cake washed with some additional ether), and the filtrate was concentrated in vacuo. The residual oil was flash chromatographed on silica gel (elution with 2:1 and then 1:1 hexane-EtOAc) to yield 786 mg (49%) of a golden-orange oil; satisfactory purity by TLC in 1:1 hexane-EtOAc. 500 MHz $^1$H NMR ($CDCl_3$) was consistent with the assigned structure. Mass spectrum ($PB-NH_3/CI$): m/e=249.1 (M+H)$^+$.

Step 6.2C (±)-3-(4-aminophenyl)-1-ethyl-3-methylpyrrolidin-2-one

A mixture of 770 mg (3.1 mmol) (±)-1-ethyl-3-methyl-3-(4-nitrophenyl)pyrrolidin-2-one, 50 mg of 10% palladium on carbon, and 50 mL of absolute ethanol was shaken with hydrogen (initial hydrogen pressure 46 psig) in a pressure vessel for 2.5 hours. The catalyst was removed by filtration through Celite under nitrogen, and the filter cake was washed with additional ethanol. Concentration of the filtrate in vacuo gave 684 mg (quantitative) of an extremely pale pink oil; essentially homogeneous by TLC in 1:1 hexane-EtOAc. 500 MHz $^1$H NMR ($CDCl_3$) was consistent with the assigned structure. Mass spectrum ($PB-NH_3/CI$): m/e=219.1 (M+H).

Step 6.2D (±)-1-ethyl-3-(4-hydrazinophenyl)-3-methylpyrrolidin-2-one

A solution of 676 mg (3.1 mmol) of (±)-3-(4-aminophenyl)-1-ethyl-3-methylpyrrolidin-2-one (from Step 3) in 3.1 mL of concentrated hydrochloric acid was then stirred at about −5° C. in an ice-acetone bath as a solution of 222 mg (3.2 mmol) of sodium nitrite in 1.25 mL of water was added dropwise over about 15 minutes. Stirring was continued at −10° to −5° C. for 45 minutes. The mixture was kept cold and added gradually to a solution of 3.50 g (15.5 mmol) of stannous chloride dihydrate in 2.5 mL of concentrated hydrochloric acid stirred under nitrogen at <0° C. in an ice-acetone bath. After completion of the addition, stirring was continued in the cooling bath for about 30 minutes, and then the mixture was partitioned between 25 mL of ethyl acetate and 4 mL of water. The aqueous layer was washed with an additional 10 mL of ethyl acetate. The combined ethyl acetate fractions were treated cautiously with 25 mL of saturated aqueous sodium carbonate solution, resulting in heavy precipitation and some gas evolution. After dilution with additional ethyl acetate and water, the mixture was filtered. The filtrate was transferred to a separatory funnel, and the ethyl acetate layer was washed with saturated aqueous sodium chloride solution. The organic phase was then dried over magnesium sulfate, filtered, and concentrated in vacuo at room temperature to yield 396 mg (55%) of a viscous, yellow oil; primarily one spot by TLC in 95:5 $CH_2Cl_2$. 500 MHz $^1$H NMR ($CDCl_3$) was consistent with the assigned structure.

Step 6.2E (±)-3-[3-(2-aminoethyl)-2-(3,5-dimethylphenyl)-1H-indol-5-yl]- 1-ethyl-3-methylpyrrolidin-2-one A solution of 395 mg (1.7 mmol) of (±)-1-ethyl-3-(4-hydrazinophenyl)-3-methylpyrrolidin-2-one and 359 mg (1.7 mmol) of 3-chloropropyl 3,5-dimethylphenyl ketone (EXAMPLE 4) in 7 mL of absolute ethanol was stirred at reflux under nitrogen for 60 hours. The solution was then cooled and concentrated in vacuo. Purification of the residue by flash chromatography on silica gel (elution with 95:5 $CH_2Cl_2$-MeOH followed by 95:5:0.5 $CH_2Cl_2$-MeOH-concd. $NH_4OH$) gave 71.4 mg of impure product, which was further purified on 4 Analtech tapered silica gel preparative TLC plates (developed in 95:5:0.5 $CH_2Cl_2$-MeOH-concd. $NH_4OH$ and the product band extracted with the same solvent) provided 38.4 mg (5.8%) of pale orange, stiff gum; virtually homogeneous by TLC in 90:10:1 $CH_2Cl_2$-MeOH-concd. $NH_4OH$. 500 MHz $^1H$ NMR ($CDCl_3$) was consistent with the assigned structure. Mass spectrum (PB-$NH_3$/CI): m/e=390.1 (M+H).

Step 6.2F (±)-N-[4-[4-[2-[2-(3,5-dimethylphenyl)-5-(1-ethyl-3-methyl-2-oxopyrrolidin-3-yl)-1H-indol-3-yl]ethylamino]-butyl]phenyl]methanesulfonamide A mixture of 37.0 mg (0.095 mmol) of (±)-3-[3-(2-aminoethyl)-2-(3,5-dimethylphenyl)-1H-indol-5-yl]-1-ethyl-3-methylpyrrolidin-2-one (from Step 5), 25.3 mg (0.105 mmol) of 4-[4-(methanesulfonamido)phenyl]butyraldehyde (EXAMPLE 4), and 57.0 mg (0.475 mmol) of anhydrous magnesium sulfate was purged with nitrogen and cooled in an ice-methanol bath at about −10° to −5° C. as 0.300 mL of dry $CDCl_3$ was added gradually by syringe. The mixture was stirred under nitrogen at this temperature for 15–20 minutes. The septum was removed just long enough to add 4.5 mg (0.12 mmol) of sodium borohydride, and the solution was repurged with nitrogen. The mixture was stirred at −10° to −5° C. as 0.200 mL of dry methanol was added gradually, and stirring was continued at this temperature. After 25 minutes, the mixture was partitioned between 5 mL of ethyl acetate and 5 mL of water. The ethyl acetate layer was washed with brine, then dried over sodium sulfate, filtered, and concentrated in vacuo. The residue was purified by preparative TLC on Analtech tapered silica gel GF plates (developed in 92.5:7.5:0.75 $CH_2Cl_2$-MeOH-concd. $NH_4OH$). Isolation of the product band (by extraction with the same solvent) gave 32.3 mg (55%) of a pale yellow, stiff foam; homogeneous by TLC in 92.5:7.5:0.75 $CH_2Cl_2$-MeOH-concd. $NH_4OH$. 500 MHz $^1H$ NMR ($CDCl_3$) was consistent with the assigned structure. Mass spectrum (ESI): m/e=615.4 (M+H).

EXAMPLE 6.3

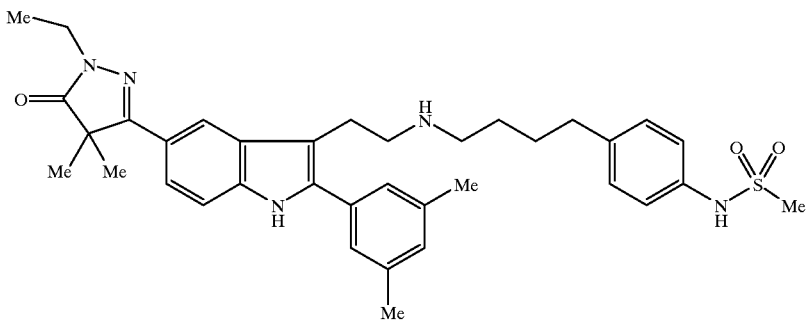

N-[4-[4-[2-[2-(3,5-dimethylphenyl)-5-(1-ethyl-4,4-dimethyl-5-oxo-4,5-dihydro-1H-pyrazol-3-yl)-1H-indol-3-yl]ethylamino]butyl]phenyl]-methanesulfonamide Step 6.3A 2-ethyl-4,4-dimethyl-5-(4-nitrophenyl)-2,4-dihydropyrazol-3-one A mixture of 1.00 g (4 mmol) of 2,2-dimethyl-3-(4-nitrophenyl)-3-oxopropionic acid methyl ester (Yang, C.-Y.; Wnek, G. E., *Polymer*, 1992, 33, 4191–4196), 3.00 g (20 mmol) of ethylhydrazine oxalate, 8 mL of 2-methoxyethanol, and 4 mL of glacial acetic acid was stirred under nitrogen at gentle reflux for 24 hours. The cooled solution was concentrated in vacuo. The residue was partitioned between ethyl acetate and water. The ethyl acetate phase was washed with additional water and then with saturated aqueous sodium chloride solution. The organic solution was dried over magnesium sulfate, filtered, and concentrated in vacuo to give 703 mg (67%) of light yellow crystals, mp 121°–122° C.; homogeneous by TLC in 2:1 hexane-EtOAc. 500 MHz $^1H$ NMR ($CDCl_3$) was consistent with the assigned structure. Mass spectrum (PB-$NH_3$/CI): m/e=265.1 (M+H).

Step 6.3B 5-(4-aminophenyl)-2-ethyl-4,4-dimethyl-2,4-dihydropyrazol-3-one

Hydrogenation of 2ethyl-4,4-dimethyl-5-(4-nitrophenyl)-2,4-dihydropyrazol-3-one according to the procedure of Example 6.2, Step C, afforded a quantitative yield of light yellow-tan solid, mp 118°–120.5° C.; homogeneous by TLC in 1:1 hexane-EtOAc and 98:2 $CH_2Cl_2$-MeOH. 500 MHz $^1H$ NMR ($CDCl_3$) was consistent with the assigned structure. Mass spectrum (ESI): m/e=232.1 (M+H).

Step 6.3C 2-ethyl-5-(4-hydrazinophenyl)-4,4-dimethyl-2,4-dihydropyrazol-3-one

This material was prepared from 5-(4-aminophenyl)-2-ethyl-4,4-dimethyl-2,4-dihydropyrazol-3-one according to the procedure of Example 6.2, Step D, except that the entire reaction mixture from the stannous chloride reduction was stirred in an ice bath and treated cautiously with excess saturated sodium carbonate solution, resulting in precipitation. This material was transferred to a separatory funnel and shaken with 2:1 ethyl acetate-methylene chloride. The mixture was filtered before separation of the phases. The aqueous phase was extracted further with several portions of ethyl acetate. The combined organic fractions were concentrated in vacuo to give an 80% yield of an amorphous, light yellow-orange solid, mp 131.5°–135° C. dec; ill-defined by TLC in 95:5 $CH_2Cl_2$-MeOH. 500 MHz $^1H$ NMR ($CDCl_3$) was consistent with the assigned structure.

Step 6.3D 5-[3-(2-aminoethyl)-2-(3,5-dimethylphenyl)-1H-indol-5-yl]-2-ethyl-4,4-dimethyl-2,4-dihydropyrazol-3-one This compound was prepared from 2-ethyl-5-(4-hydrazinophenyl)-4,4-dimethyl-2,4-dihydropyrazol-3-one and 3-chloropropyl 3,5-dimethylphenyl ketone (EXAMPLE 4) according to the procedure of Example 6.2, Step E, except that the reaction time was 15 hours. Flash chromatography of the crude product on silica gel (gradient elution with 97:3 and 95:5 $CH_2Cl_2$-MeOH followed by 95:5:0.5 and 92.5:7.5:0.75 CH₂Cl₂-MeOH-concd. NH₄OH) gave a 27% yield of light tan, stiff foam; homogeneous by TLC in 92.5:7.5:0.75 CH₂Cl₂-MeOH-concd. NH₄OH. 500 MHz ¹H NMR (CDCl₃) was consistent with the assigned structure. Mass spectrum (PB-NH₃/CI): m/e=403.2 (M+H)⁺.

Step 6.3E N-[4-[4-[2-[2-(3,5-dimethylphenyl)-5-(1-ethyl-4,4-dimethyl-5-oxo-4,5-dihydro-1H-pyrazol-3-yl)-1H-indol-3-yl]ethylamino]butyl]phenyl]methanesulfonamide Reductive amination of 4-[4-(methanesulfonamido)phenyl] butyraldehyde (EXAMPLE 4) with 5-[3-(2-aminoethyl)-2-(3,5-dimethylphenyl)-1H-indol-5-yl]-2-ethyl-4,4-dimethyl-2,4-dihydropyrazol-3-one was carried out according to the method of Example 6.2, Step F, except that 90:10 CH₂Cl₂-MeOH was used to develop the preparative TLC plates, while 90:10:1 CH₂Cl₂-MeOH-concd. NH₄OH was used to extract the product. This gave a 55% yield of very pale golden-yellow glass; homogeneous by TLC in 92.5:7.5 CH₂Cl₂-MeOH. 500 MHz ¹H NMR (CDCl₃) was consistent with the assigned structure. Mass spectrum (ESI): m/e=628.5 (M+H)⁺.

Following a procedure similar to that described in EXAMPLE 6.1, the following compounds were prepared:

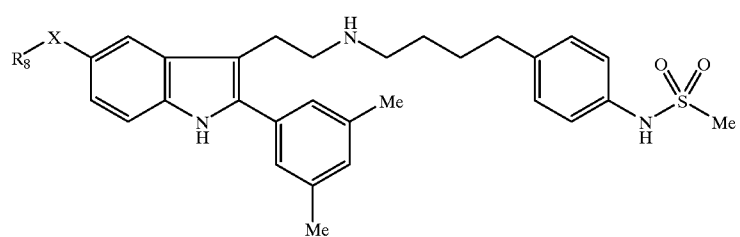

| Example | X-R₈ | m/e |
|---|---|---|
| 6A | | 657 (M + H) |
| 6B | | 629 (M + H) |
| 6C | | 645 (M + H) |

EXAMPLE 7.1

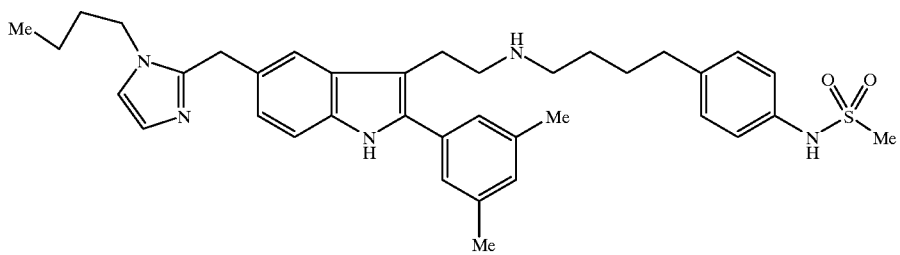

N-[4-[4-[4-[2-[5-(1-butyl-1H-imidazol-2-ylmethyl)-2-(3,5-dimethylphenyl)-1H-indol-3-yl]ethylamino]butyl]phenyl]methane-sulfonamide Step 7.1A 1-butyl-2-(4-nitrobenzyl)-1H-imidazole A solution of 6.13 g (25 mmol) of ethyl 4-nitrophenylacetimidate hydrocholoride (Forsyth, R. and Pyman, F. L., J. Chem. Soc., 1930, 397) and 8.05 g (50 mmol) of 2-(butylamino)acetaldehyde dimethyl acetal (Jones, R. G. et al., J. Am. Chem. Soc., 1949, 71, 4000; Kaye, I. A. and Minsky, I., J. Am. Chem. Soc., 1949, 71, 2272) in 50 mL of ethanol was stirred at reflux under nitrogen for 20 hours. The solution was then cooled and concentrated in vacuo. The residue was treated with 50 mL of 2N hydrochloric acid, agitated for several minutes, and then extracted with a mixture of 50 mL of diethyl ether and 10 mL of tetrahydrofuran. The filtered aqueous phase was stirred at 60° C. under nitrogen for 4 hours. The cooled solution was concentrated in vacuo, and the residue was partitioned between 100 mL of ether and 50 mL of saturated sodium bicarbonate solution (CAUTION: foaming). The mixture was filtered before separation of the phases. The organic phase was concentrated and purified by column chromatography on silica gel (gradient elution with 0.5–2% MeOH in $CH_2Cl_2$) to give 1.62 g (25%) of a dark reddish oil; satisfactory purity by TLC in 95:5 $CH_2Cl_2$-MeOH. 300 MHz $^1$H NMR ($CDCl_3$) was consistent with the assigned structure. Mass spectrum (FAB): m/e=260 (M+H.

Step 7.1B 4-(1-butyl-1H-imidazol-2-ylmethyl)phenylamine

A solution of 259 mg (1 mmol) of 1-butyl-2-(4-nitrobenzyl)-1H-imidazole in 3 mL of tetrahydrofuran was stirred in an ice bath as a solution of 1.36 g (6 mmol) of stannous chloride dihydrate in 1.8 mL of concentrated hydrochloric acid was added dropwise over 3–4 minutes. The ice bath was removed, and the mixture was stirred under nitrogen at room temperature for 3.5 hours. It was then added to a mixture of 9 mL of 50% sodium hydroxide and approximately 35 g of ice. After agitation for 2–3 minutes, the product was extracted with 50 mL of diethyl ether. The organic phase was dried (sodium sulfate), filtered, and concentrated in vacuo. Trituration of the residue with a small amount of ether gave a crystalline solid, which was collected on a filter and washed with petroleum ether to give 156 mg (68%) of pale, yellow-tan crystals, mp 107°–108° C.; homogeneous by TLC in 90:10 $CH_2Cl_2$-MeOH. 300 MHz $^1$H NMR ($CDCl_3$) was consistent with the assigned structure. Mass spectrum (FAB): m/e 230 (M+H)$^+$. Analysis ($C_{14}H_{19}N_3$) Calcd.: C, 73.32; H, 8.35; N, 18.32. Found: C, 73.11; H, 8.30; N, 18.10. The identical product was also obtained by hydrogenation of the nitro compound in EtOH in the presence of 10% palladium on carbon catalyst.

Step 7.1C [4-(1-butyl-1H-imidazol-2-ylmethyl)phenyl]hydrazine

A solution of 383 mg (1.67 mmol) of 4-(1-butyl-1H-imidazol-2-ylmethylphenylamine in 1 mL of concentrated hydrochloric acid was stirred at about –10° C. as a solution of 115 mg (1.67 mmol) of sodium nitrite in 0.7 mL of water was added dropwise. Stirring was continued –10° to 0° C. for 30 minutes. The mixture was kept cold and added gradually to a solution of 132 g (5.85 mmol) of stannous chloride dihydrate in 1.2 mL of concentrated hydrochloric acid stirred under nitrogen at –10°. After completion of the addition, stirring was continued in the cooling bath for about 5 minutes, and then the mixture was allowed to warm to room temperature. The mixture was again cooled, basified with 50% sodium hydroxide, and filtered. The filtrate was diluted with some 5N sodium hydroxide and extracted repeatedly with tetrahydrofuran. The combined tetrahydrofuran extracts were dried over sodium sulfate, filtered, and concentrated in vacuo to give 350 mg (86%) of a brown liquid, which was satisfactory for use in the next step.

Step 7.1D 2-[5-(1-butyl-1H-imidazol-2-ylmethyl)-2-(3,5-dimethylphenyl)-1H-indol-3-yl]ethylamine A solution of 350 mg (1.43 mmol) of (4-(1-butyl-1H-imidazol-2-ylmethyl)phenyl]hydrazine and 362 mg (1.72 mmol) of 3-chloropropyl 3,5-dimethylphenyl ketone (EXAMPLE 4) in 3 mL of 2-methoxyethanol was stirred at reflux under nitrogen for 3 hours. The solution was then cooled and concentrated in vacuo. Purification of the residue by flash chromatography on silica gel (elution with 95:5 $CH_2Cl_2$-MeOH followed by 95:5:0.5 $CH_2Cl_2$-MeOH-concd. $NH_4OH$) gave 50 mg (9%) of material that was satisfactory for use in the next step.

Step 7.1E N-[4-[4-[2-[5-(1-Butyl-1H-imidazol-2-ylmethyl)-2-(3,5-dimethylphenyl)-1H-indol-3-yl]ethylamino]butyl]phenyl]-methanesulfonamide A mixture of 50 mg (0.125 mmol) of 2-[5-(1-butyl-1H-imidazol-2-ylmethyl)-2-(3,5-dimethylphenyl)-1H-indol-3-yl]ethylamine, 33 mg (0.105 mmol) of 4-[4-(methanesulfonamido)phenyl] butyraldehyde (EXAMPLE 4), 75 mg (0.625 mmol) of anhydrous magnesium sulfate, and 0.800 mL of dry $CDCl_3$ was stirred under nitrogen at –10° C. for 30 minutes. The septum was removed just long enough to add 6.1 mg (0.163 mmol) of sodium borohydride. The solution was stirred at –10° to –5° C. as 0.200 mL of dry methanol was added gradually, and stirring was continued at about –5° C. After 30 minutes, the mixture was partitioned between 5 mL of ethyl acetate and 5 mL of water (basified to pH 10). The ethyl acetate layer was washed with brine, then dried over sodium sulfate, filtered, and concentrated in vacuo. The residue was purified by flash chromatography on silica gel (gradient elution with 5–10% MeOH in $CH_2Cl_2$). Further purification on a 1000-micron silica gel GF preparative TLC plate (developed in 90:10 CH$_2$Cl$_2$-MeOH) afforded 1.4 mg (1.8%) of a white solid, mp 90°–92° C.; homogeneous by TLC in 90:10 CH$_2$Cl$_2$-MeOH. 500 MHz $^1$H NMR (CDCl$_3$) was consistent with the assigned structure. Mass spectrum (ESI): m/e=626.5 (M+H).

EXAMPLE 7.2

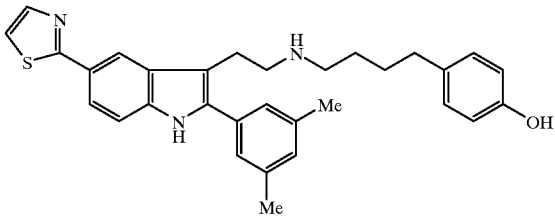

4-[4-[2-[2-(3,5-dimethylphenyl)-5-thiazol-2-yl-1H-indol-3-yl]ethylamino]butyl]phenol Step 7.2A (4-thiazol-2-ylphenyl)hydrazine By the procedure of Example 7.1, Step C, 4-thiazol-2-ylphenylamine [may be prepared according to the methods of Example 7.1, Step B, by reduction of 2-(4-nitrophenyl) thiazole (Belen'kii, L. I., et al., *Chem. Scr.*, 1985, 25, 295–299)] was diazotized and reduced with stannous chloride. In this case, the precipitate obtained after basification with 50% sodium hydroxide was isolated by filtration and leached with warm methylene chloride. The filtered methylene chloride solution was concentrated in vacuo to give a 44% yield of material satisfactory for use in the next step.

Step 7.2B 2-[2-(3,5-dimethylphenyl)-5-thiazol-2-yl-1H-indol-3-yl]ethylamine

Reaction of (4-thiazol-2-ylphenyl)hydrazine and 3-chloropropyl 3,5-dimethylphenyl ketone (EXAMPLE 4) was carried out according to the procedure of Example 7.1, Step D to give a 14% yield of the title compound as a yellow, stiff foam, mp 98.5°–100.5° C.; homogeneous by TLC in 95:5 CH$_2$Cl$_2$-MeOH. 500 MHz $^1$H NMR (CDCl$_3$) was consistent with the assigned structure. Mass spectrum (PB-NH$_3$/CI): m/e=348.2 (M+H).

Step 7.2C N-[2-[2-(3,5-dimethylphenyl)-5-thiazol-2-yl-1H-indol-3-yl]ethyl]-4-(4-hydroxyphenyl)butyramide To a suspension of 100 mg (0.288 mmol) of 2-[2-(3,5-dimethylphenyl)-5-thiazol-2-yl-1H-indol-3-yl]ethylamine in 1.4 mL of dry methylene chloride were added 69.0 mg (0.360 mmol) of 1-(3-dimethylaminopropyl)-3-ethylcarbodiimide (EDC) and 52.8 mg (0.391 mmol) of 1-hydroxybenzotriazole (HOBT). The solution was stirred at room temperature under nitrogen for 20 minutes. Then a solution of 64.8 mg (0.360 mmol) of 4-(4-hydroxyphenyl) butyric acid in 0.6 mL of N,N-dimethylformamide was added, gradually resulting in a homogeneous solution. After about 3 hours, the solution was concentrated in vacuo, and the residue was purified by flash chromatography on silica gel (gradient elution with 1–3% MeOH in CH$_2$Cl$_2$), providing 125 mg (85%) of a yellow solid, mp 108°–109.5° C.; homogeneous by TLC in 95:5 CH$_2$Cl$_2$-MeOH. 500 MHz $^1$H NMR (CDCl$_3$) was consistent with the assigned structure. Mass spectrum (ESI): m/e=510.1 (M+H).

Step 7.2D 4-[4-[2-[2-(3,5-dimethylphenyl)-5-thiazol-2-yl-1H-indol-3-yl]ethylamino]butyl]phenol To a solution of 120 mg (0.235 mmol) of N-[2-[2-(3,5-dimethylphenyl)-5-thiazol-2-yl-1H-indol-3-yl]ethyl]-4-(4-hydroxyphenyl)butyramide in 4 mL of dry tetrahydrofuran was added 2.12 mL (2.12 mmol) of 1M borane-tetrahydrofuran complex in tetrahydrofuran. The resulting solution was stirred at reflux under nitrogen for about 2.5 hours. It was then cooled to room temperature and quenched by gradual addition of excess methanol. The solution was then concentrated in vacuo. The residue was treated with 628 mg (7.05 mmol) of N,N-dimethylethanolamine and heated at 100° C. under nitrogen for an additional 2.5 hours. The solution was concentrated in vacuo, and the residue was flash chromatographed on silica gel (gradient elution with 2–6% MeOH in CH$_2$Cl$_2$) to give 91 mg (78%) of a white solid, mp 121°–123° C.; homogeneous by TLC in 90:10 CH$_2$Cl$_2$-MeOH. 500 MHz $^1$H NMR (CDCl$_3$+ small amount of CD$_3$OD) was consistent with the assigned structure. Mass spectrum (PB-NH$_3$/CI): m/e=496.2 (M+H).

Following a procedure similar to that described above and in EXAMPLES 2 and 4, the following compounds were prepared:

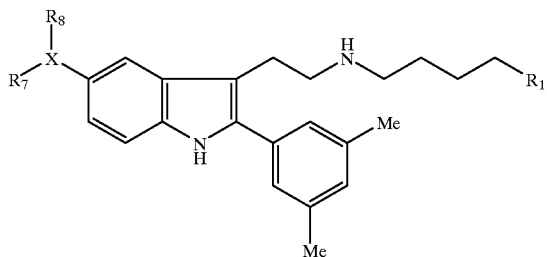

| Example | X-R$_7$R$_8$ | R$_1$ | m/e |
|---------|--------------|-------|-----|
| 7A | 4-pyridyl-CH$_2$- | Ph-4-NHSO$_2$Me | 581 (M + H) |
| 7B | 4-pyridyl-CH$_2$- | Ph-4-NHSO$_2$Me | 567 (M + H) |

-continued

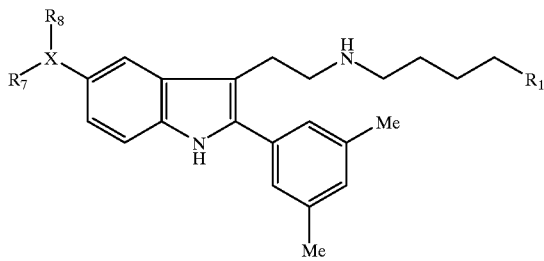

| Example | X-R₇R₈ | R₁ | m/e |
|---|---|---|---|
| 7C | Me, N-ethyl imidazole | Ph-4-NHSO₂Me | 584 (M + H) |
| 7D | benzoxazole | Ph-4-OH | 530 (M + H) |
| 7E | ethylsulfonyl piperazine N-methyl carboxamide | Ph-4-NHC(O)Me | 673 (M + H) |
| 7F | 2,5-dimethyl-1-acetyl pyrrolidine | Ph-4-SO₂N(Me)₂ | 629 (M + H) |

EXAMPLE 8.1

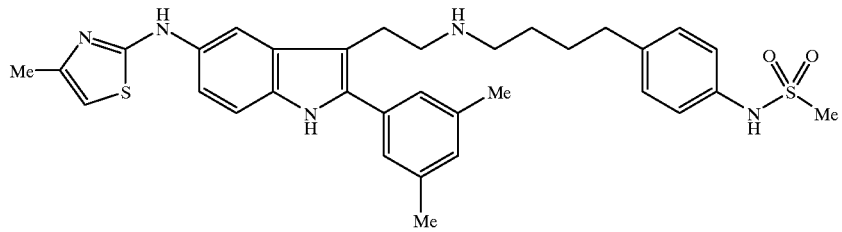

N-[4-(4-{2-[2-(3,5-dimethylphenyl)-5-(4-methylthiazol-2-ylamino)-1H-indol-3-yl]ethylamino}butylphenyl]methanesulfonamide Step 8.1A {2-[5-amino-2-(3,5-dimethylphenyl)-1H-indol-3-yl]ethyl}-[4-(4-methanesulfonylaminophenyl)butyl]carbamic acid tert-butyl ester Prepared essentially as described in EXAMPLE 2.1C starting from {2-[2-(3,5-dimethylphenyl)-5-nitro-1H-indol-3-yl]ethyl}-[4-(4-methanesulfonylaminophenyl)butyl] carbamic acid tert-butyl ester (from EXAMPLE 3.2A, 300 mg) to give the title compound (217 mg).

Step 8.1B {2-[2-(3,5-dimethylphenyl)-5-thioureido-1H-indol-3-yl]ethyl}-4-(4-methanesulfonylaminophenyl) butyl] carbamic acid tert-butyl ester To a solution of {2-[5-amino-2-(3,5-dimethylphenyl)-1H-indol-3-yl]ethyl}-[4-(4-methanesulfonylaminophenyl) butyl]carbamic acid tert-butyl ester (157 mg in 7 mL dry tetrahydrofuran) at 0° C. was added 57 mg 1,1'-thicarbonyldiimidazole and the stirred mixture allowed to warm to room temperature. After 30 minutes, the mixture was cooled to 0° C. and 4 mL of ammonia saturated methylene chloride was added via syringe and the mixture again warmed to room temperature. After 19 hours, the reaction was quenched by the addition of saturated aqueous ammonium chloride and the mixture extracted with ethyl acetate. The organic portion was washed successively with saturated ammonium chloride and brine then dried over sodium sulfate. The concentrate was purified by flash chromatography on silica gel (methylene chloride:methanol, 95:5) to give the title compound (161 mg).

Step 8.1C {2-[2-(3,5-dimethylphenyl)-5-(4-methylthiazol-2-ylamino)-1H-indol-3yl]-ethyl}-[4-(4-methanesulfonylaminophenyl) butyl]carbamic acid tert-butyl ester To a solution of {2-[2-(3,5-dimethylphenyl)-5-thioureido-1H-indol-3-yl]ethyl}-[4-(4-methanesulfonylaminophenyl) butyl]carbamic acid tert-butyl ester (15 mg in 0.80 mL ethanol) was added 0.010 mL chloroacetone and the resulting suspension heated to reflux on an oil bath. After 5 hours, the mixture was cooled to room temperature and concentrated in vacuo. Purification of the residue by flash chromatography on silica gel (methylene chloride:methanol, 96:4) gave the title compound (15 mg).

Step 8.1D N-[4-(4-{2-[2-(3,5-dimethylphenyl)-5-(4-methylthiazol-2-ylamino)-1H-indol-3-yl]ethylamino}butyl) phenyl] methanesulfonamide Prepared essentially as described in EXAMPLE 3.2G starting from {2-[2-(3,5-dimethylphenyl)-5-(4-methlthiazol-2-ylamino)-1H-indol-3-yl]-ethyl}-[4-(4-methanesulfonylaminophenyl) butyl]carbamic acid tert-butyl ester (15 mg) to give the title compound (13 mg). m/e=602 (M+H)

EXAMPLE 8.2 anhydride and the mixture stirred at low temperature. After 15 minutes, the reaction was quenched by the addition of saturated aqueous sodium bicarbonate and extracted with ethyl acetate. The organic portion was washed successively with a pH2 solution, saturated sodium bicarbonate and brine, then dried over sodium sulfate. Concentration in vacuo provided the crude title compound (65 mg).

Step 8.2B {2-[2-(3,5-dimethylphenyl)-5-(5-methyltetrazol-1-yl)-1H-indol-3-yl]-ethyl}-[4-(4-amino (dimethanesulfonyl)phenyl) butyl]carbamic acid tert-butyl ester To a solution of {2-[5-acetylamino-2-(3,5-dimethylphenyl)-1H-indol-3-yl]ethyl}-[4-(4-amino (dimethanesulfonyl)phenyl)butyl] carbamic acid tert-butyl ester (30 mg in 1.5 mL dry methylene chloride) was added in order 22.8 mg triphenylphosphine, 6.3 mg imidazole, 20.7 mg zinc azide(pyridine complex) and 0.014 mL diethyl azodicarboxylate and the mixture stirred at room temperature. After 4 hours additional portions of triphenylphosphine (11.3 mg), imidazole (3.5 mg), zinc azide•2 pyridine (11 mg) and diethyl azodicarboxylate (0.007 mL) were added and the mixture heated to reflux on an oil bath. After an additional 3 hours reaction time, the pot was cooled to room temperature and the reaction mixture applied directly to a silica gel column for purification by flash chromatography (hexane:ethyl acetate, 2:3) to give the title compound (26 mg).

Step 8.2C {2-[2-(3,5-dimethylphenyl)-5-(5-methyltetrazol-1-yl)-1H-indol-3-yl]-ethyl}-[4-(4-methanesulfonylaminophenyl)butyl] carbamic acid tert-butyl ester Prepared essentially as described in EXAMPLE 3.2F starting from {2-[2-(3,5-dimethylphenyl)-5-(5-

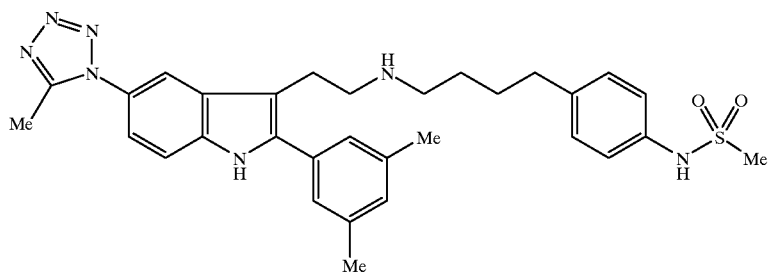

N-[4-(4-{2-[2-(3,5-dimethylphenyl)-5-(5-methyltetrazol-1-yl)-1H-indol-3-yl] ethylamino}butyl)phenyl]methanesulfonamide Step 8.2A {2-[5-acetylamino-2-(3,5-dimethylphenyl)-1H-indol-3-yl]ethyl}-[4-(4-amino(dimethanesulfonyl) phenyl)butyl] carbamic acid tert-butyl ester To a solution of {2-[5-amino-2-(3,5-dimethylphenyl)-1H-indol-3-yl]ethyl}-[4-(4-amino(dimethanesulfonyl)phenyl) butyl] carbamic acid tert-butyl ester (from EXAMPLE 3.2 StepC, 60 mg in 3 mL dry methylene chloride) at 0° C. was added 0.025 mL pyridine followed by 0.020 mL acetic methyltetrazol-1-yl)-1H-indol-3-yl]-ethyl}-[4-(4-amino (dimethanesulfonyl)phenyl) butyl]carbamic acid tert-butyl ester (26 mg) to give the title compound (23 mg).

Step 8.2D N-[4-(4-{2-[2-(3,5-dimethylphenyl)-5-(5-methyltetrazol-1-yl)-1H-indol-3-yl]ethylamino}butyl) phenyl]methane sulfonamide Prepared essentially as described in EXAMPLE 3.2G starting from {2-[2-(3,5-dimethylphenyl)-5-(5-methyltetrazol-1-yl)-1H-indol-3-yl]-ethyl}-[4-(4-methanesulfonylaminophenyl)butyl]carbamic acid tert-butyl ester (23 mg) to give the title compound (18 mg). m/e=572 (M+H)

EXAMPLE 8.3

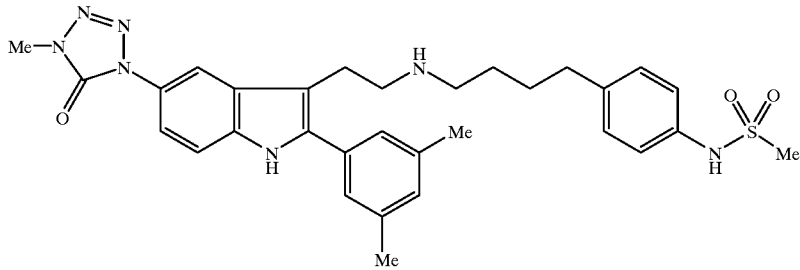

N-[4-(4-{2-[2-(3,5-dimethylphenyl)-5-(4-methyl-5-oxo-4,5-dihydro-tetrazol-1yl)-1H-indol-3-yl]ethylamino}butyl)phenyl]methanesulfonamide Step 8.3A N,N-{4-[4-(benzyl-{2-[2-(3,5-dimethylphenyl)-5-nitro-1H-indol-3-yl]ethyl}amino)butyl]phenyl}dimethanesulfonamide Prepared essentially as described in EXAMPLE 3.2B starting from N-{4-[4-(benzyl-{2-[2-(3,5-dimethylphenyl)-5-nitro-1H-indol-3-yl]ethyl}amino)butyl]phenyl} methanesulfonamide (EXAMPLE 2.1 StepB, 300 mg) to give the title compound (338 mg).

Step 8.3B N,N-{4-[4-(benzyl-{2-[2-(3,5-dimethylphenyl)-5-amino-1H-indol-3-yl]ethyl}amino)butyl]phenyl} dimethanesulfonamide Prepared essentially as described in EXAMPLE 2.1 StepC starting from N,N-{4-[4-(benzyl-{2-[2-(3,5-dimethylphenyl)-5-nitro-1H-indol-3-yl]ethyl}amino)butyl]phenyl} dimethanesulfonamide (338 mg) to give the title compound (254 mg).

Step 8.3C N,N-{4-[4-(benzyl-{2-[2-(3,5-dimethylphenyl)-5-isocyanato-1H-indol-3-yl]ethyl}amino)butyl]phenyl} dimethanesulfonamide Prepared essentially as described in EXAMPLE 3.2 StepD starting from N,N-{4-[4-(benzyl-{2-[2-(3,5-dimethylphenyl)-5-amino-1H-indol-3-yl]ethyl}amino)butyl]phenyl} dimethanesulfonamide (120 mg) to give the title compound (88 mg).

Step 8.3D N,N-{4-[4-(benzyl-{2-[2-(3,5-dimethylphenyl)-5-(5-oxo-4,5-dihydro-tetrazol-1-yl)-1H-indol-3-yl]ethyl}amino)butyl]phenyl}dimethanesulfonamide To a solution of freshly prepared aluminum azide (0.24 mmol in 5 mL dry tetrahydrofuran) was added 88 mg N,N-{4-[4-(benzyl-{2-[2-(3,5-dimethylphenyl)-5-isocyanato-1H-indol-3-yl]ethyl}amino)butyl]phenyl}dimethanesulfonamide and the mixture heated to reflux on an oil bath. After 23 hours, the mixture was cooled to room temperature and poured into a mixture of 1M sodium potassium tartarate and ice, stirred vigorously for 20 minutes then partitioned between ethyl acetate and water. The organic portion was washed successively with 1M sodium potassium tartarate, saturated ammonium chloride and brine then dried over sodium sulfate. Purification of the concentrate by flash chromatography on silica gel (methylene chloride:methanol, 91:9) gave the title compound (17 mg).

Step 8.3E N,N-{4-[4-(benzyl-{2-[2-(3,5-dimethylphenyl)-5-(4-methyl-5-oxo-4,5-dihydrotetrazol-1yl)-1H-indol-3-yl]ethyl}amino)butyl]phenyl}dimethanesulfonamide To a solution of N,N-{4-[4-(benzyl-{2-[2-(3,5-dimethylphenyl)-5-(5-oxo-4,5-dihydro-tetrazol-1-yl)-1H-indol-3-yl]ethyl}amino)butyl]phenyl}dimethanesulfonamide (35 mg in 2 mL dry N,N-dimethylformamide) was added 70 mg potassium carbonate followed by 0.015 mL iodomethane and the mixture stirred at room temperature. After 50 minutes, the reaction was quenched by the addition of saturated aqueous ammonium chloride and the mixture extracted with ethyl acetate. The organic portion was washed successively with water and brine, dried over sodium sulfate and concentrated in vacuo. Purification of the concentrate by flash chromatography on silica gel (hexane:ethyl acetate, 2:3) gave the title compound (26 mg).

Step 8.3F N-{4-[4-(benzyl-{2-[2-(3,5-dimethylphenyl)-5-(4-methyl-5-oxo-4,5-dihydrotetrazol-1-yl)-1H-indol-3-yl]ethyl}amino)butyl]phenyl}methanesulfonamide Prepared essentially as described in EXAMPLE 3.2F starting from N,N-{4-[4-(benzyl-{2-[2-(3,5-dimethylphenyl)-5-(4-methyl-5-oxo-4,5-dihydrotetrazol-1-yl)-1H-indol-3-yl]ethyl}amino)butyl]phenyl}-dimethanesulfonamide (26 mg) to give the title compound (23 mg).

Step 8.3G N-[4-(4-{2-[2-(3,5-dimethylphenyl)-5-(4-methyl-5-oxo-4,5-dihydro-tetrazol-1-yl)-1H-indol-3-yl]ethylamino}butyl)phenyl]methanesulfonamide The title compound was prepared essentially as described in EXAMPLE 2.1 StepE starting from N-{4-[4-(benzyl-{2-[2-(3,5-dimethylphenyl)-5-(4-methyl-5-oxo-4,5-dihydrotetrazol-1-yl)-1H-indol-3-yl]ethyl}amino)butyl]phenyl}methanesulfonamide (23 mg) to give the title compound (16 mg). m/e=588 (M)

Following a procedure similar to that described above, the following compounds were prepared:

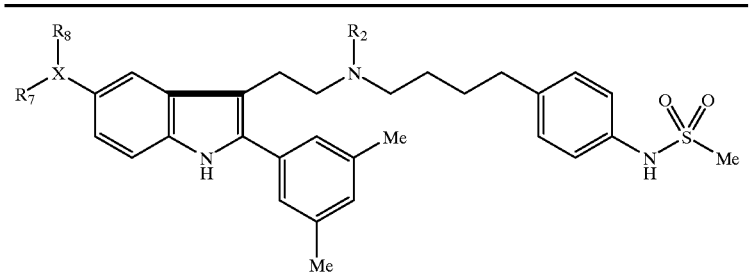
| Example | X-R₇R₈ | R₂ | m/e |
|---|---|---|---|
| 8A | 4-ethyl-5-methyl-2-(methylamino)thiazole | —H | 630 (M + H) |
| 8B | 4-tert-butyl-2-(methylamino)thiazole | —H | 644 (M + H) |
| 8C | 1-methyltetrazole | —H | 558 (M + H) |
| 8D | 1-methyl-5-isobutyltetrazole | —H | 614 (M + H) |
| 8E | 4-methyl-5-oxo-tetrazoline | —H | 574 (M + H) |
| 8F | 1,4-dimethyl-5-oxo-tetrazoline | —Me | 602 (M + H) |
| 8G | 1-butyl-4-methyl-5-oxo-tetrazoline | —H | 630 (M + H) |

What is claimed is:

1. A compound of the formula

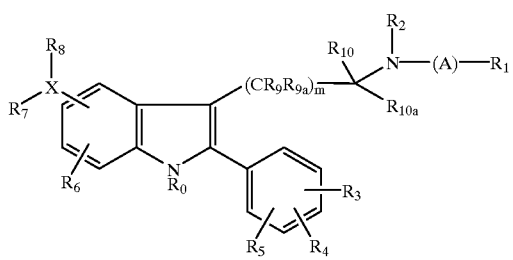

(I)

wherein

A is $C_1$–$C_6$ alkyl;
$R_0$ is hydrogen;
$R_1$ is

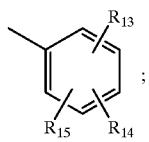

;

$R_2$ is hydrogen or $C_1$–$C_6$ alkyl;
$R_3$, $R_4$ and $R_5$ are independently hydrogen or $C_1$–$C_6$ alkyl, said alkyl group optionally substituted with hydroxy, oxo or cyano;
$R_6$ is hydrogen or $C_1$–$C_6$ alkyl, said alkyl group optionally substituted with hydroxy, oxo or cyano;
$R_7$ is hydrogen;
$R_8$ is 7-azabicylco[2.2.1] heptane;
$R_9$ and $R_{9a}$ are independently $C_1$–$C_6$ alkyl;
$R_{10}$ and $R_{10a}$ are hydrogen;
$R_{13}$ is hydrogen or $NHSO_2(C_1$–$C_6$ alkyl);
$R_{14}$ and $R_{15}$ are hydrogen;
X is C(O);
or a pharmaceutically acceptable addition salt and/or hydrate thereof, or where applicable, a geometric or optical isomer or racemic mixture thereof.

2. A pharmaceutical composition which comprises an effective amount of a compound as defined in claim 1 and a pharmaceutically acceptable carrier therefor.

3. A method for antagonizing gonadotropin-releasing hormone in a subject in need thereof which comprises administering to said subject an effective amount of a compound as defined in claim 1 to a subject suffering from a gonadotropin-releasing hormone derived disorder.

4. A method according to claim 3 wherein the gonadotropin-releasing hormone derived disorder is a sex-hormone related condition.

5. A method according to claim 4 wherein the sex hormone related condition is selected from the group consisting of endometriosis, polycystic ovarian disease, uterine fibroids and precocious puberty.

6. A pharmaceutical composition which comprises an inert carrier and an effective amount of a compound which stimulates the endogenous production or release of growth hormone in combination with a compound as defined in claim 1.

7. A pharmaceutical composition made by combining the compound of claim 1 and a pharmaceutically acceptable carrier therefor.

8. A process for making a pharmaceutical composition comprising combining a compound of claim 1 and a pharmaceutically acceptable carrier.

9. The compound according to claim 1 of the formula

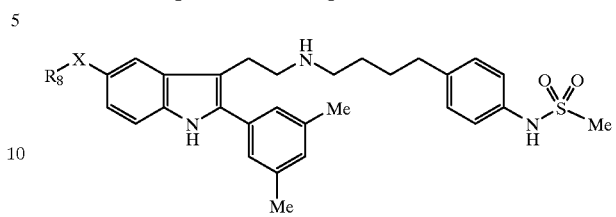

wherein X-$R_8$ is as indicated in the table below:

| X—$R_8$ |
|---|
|  | or a pharmaceutically acceptable addition salt and/or hydrate thereof, or where applicable, a geometric or optical isomer or racemic mixture thereof.

10. A method according to claim 3 wherein the gonadotropin-releasing hormone derived disorder is a sex hormone dependent cancer, benign prostatic hypertropy or myoma of the uterus.

11. A method according to claim 10 wherein the sex hormone dependent cancer is selected from the group consisting of prostatic cancer, uterine cancer, breast cancer and pituitary gonadotrophe adenomas.

12. A method for preventing pregnancy in a subject in need thereof which comprises administering an effective amount of a compound as defined in claim 1.

13. A method for treating lupus erythematosis in a subject in need thereof which comprises administering to said subject an effective amount of a compound as defined in claim 1.

14. A method for treating irritable bowel syndrome in a subject in need thereof which comprises administering to said subject an effective amount of a compound as defined in claim 1.

15. A method for treating premenstrual syndrome in a subject in need thereof which comprises administering to said subject an effective amount of a compound as defined in claim 1.

16. A method for treating hirsutism in a subject in need thereof which comprises administering to said subject an effective amount of a compound as defined in claim 1.

17. A method for treating short stature or a growth hormone deficiency in a subject in need thereof which comprises administering to said subject an effective amount of a compound which stimulates the endogenous production or release of growth hormone and an effective amount of a compound as defined in claim 1.

18. A method for treating sleep disorders in a subject in need thereof which comprises administering to said subject an effective amount of a compound as defined in claim 1.

19. The method of claim 18 wherein the sleep disorder is sleep apnea.

* * * * *